United States Patent [19]

Sum et al.

[11] Patent Number: 4,940,710

[45] Date of Patent: Jul. 10, 1990

[54] 7-(SUBSTITUTED)PIPERAZINYL-1-ETHYL-6-FLUORO-1,4-DIHYDRO-4-OXO-3-QUINOLINECARBOXYLIC ACIDS

[75] Inventors: Phaik-Eng Sum, New City, N.Y.; Joseph P. Joseph, Montvale, N.J.; Carl B. Ziegler, Jr., Congers, N.Y.; Daniel B. Moran, Suffern, N.Y.; Yang-I Lin, Nanuet, N.Y.

[73] Assignee: American Cyanamid Company, Stamford, Conn.

[21] Appl. No.: 81,786

[22] Filed: Aug. 5, 1987

Related U.S. Application Data

[63] Continuation-in-part of Ser. No. 940,133, Dec. 17, 1986, abandoned, which is a continuation-in-part of Ser. No. 820,279, Jan. 17, 1986, abandoned.

[51] Int. Cl.$^5$ .................. A61K 31/495; C07D 401/04
[52] U.S. Cl. ................................ 514/254; 514/234.5; 514/235.2; 544/32; 544/101; 544/121; 544/358; 544/360; 544/361; 544/362; 544/363; 544/371; 544/372; 544/373; 544/376; 544/403; 546/156
[58] Field of Search ................. 544/363, 362, 32, 101, 544/121, 361; 514/222, 254

[56] References Cited

U.S. PATENT DOCUMENTS

| | | | |
|---|---|---|---|
| 2,647,120 | 7/1953 | Williamson | 544/379 |
| 4,166,180 | 8/1979 | Kato et al. | 544/398 |
| 4,359,578 | 11/1982 | Matsumoto et al. | 544/363 |
| 4,429,127 | 1/1984 | Irikura et al. | 544/363 |
| 4,448,962 | 5/1984 | Irikura et al. | 544/363 |
| 4,544,658 | 10/1985 | Petersen et al. | 544/363 |
| 4,552,879 | 11/1985 | Ishikawa et al. | 544/363 |
| 4,563,459 | 1/1986 | Grohe et al. | 544/363 |

FOREIGN PATENT DOCUMENTS 1196721  7/1970  United Kingdom ............. 544/398

OTHER PUBLICATIONS

"Chemical Abstracts", vol. 101, 1984, col. 101:90977e.

*Primary Examiner*—Richard L. Raymond
*Assistant Examiner*—James H. Turnipseed
*Attorney, Agent, or Firm*—H. G. Jackson

[57] ABSTRACT

7-(substituted)piperazinyl-1-ethyl-6-fluoro-4-oxo-3-quinolinecarboxylic acids, the pharmacologically acceptable salts thereof, compositions containing them, processes and intermediates for producing them, and methods of using them to treat bacterial infections in warm-blooded animals.

11 Claims, No Drawings

7-(SUBSTITUTED)PIPERAZINYL-1-ETHYL-6-FLUORO-1,4-DIHYDRO-4-OXO-3-QUINOLINECARBOXYLIC ACIDS

SUMMARY OF THE INVENTION

This application is a continuation-in-part of U.S. Ser. No. 06/940,133, filed Dec. 17, 1986 which is a continuation-in-part of U.S. Ser. No. 820,279, filed Jan. 17, 1986 both now abandoned.

This invention is concerned with new compounds of the formula I:

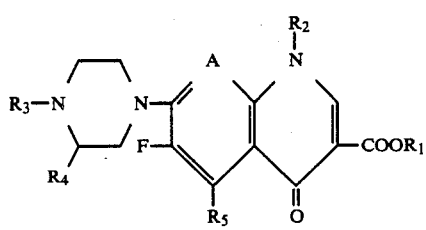

Formula I wherein $R_1$ is hydrogen, alkyl($C_1$-$C_3$), dialkyl($C_1$-$C_3$)aminoalkyl($C_1$-$C_3$), N-piperidinoalkyl($C_1$-$C_3$), N-morpholinoalkyl($C_1$-$C_3$), N-4-methylpiperidinoalkyl($C_N$-4-alkyl($C_1$-$C_3$)piperazinylalkyl($C_1$-$C_3$),

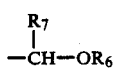

where $R_6$ is acyl or $COOR_8$, $R_8$ is alkyl($C_1$-$C_3$) and $R_7$ is hydrogen or alkyl($C_1$-$C_3$), or an alkali or alkaline earth metal; $R_2$ is alkyl($C_1$-$C_4$), cycloalkyl($C_3$-$C_6$), alkoxy($C_1$-$C_4$), alkylamino($C_1$-$C_3$), vinyl, phenyl, benzyl, —$CH_2CH_2F$ or mono- or polysubstituted phenyl (wherein the substituent is halogen, $CF_3$ or $OCH_2F$); $R_3$ is hydrogen, benzyl, or alkyl($C_1$-$C_3$); $R_4$ is hydrogen, alkyl($C_1$-$C_3$), ethenyl, ethynyl, cycloalkyl($C_3$-$C_6$), fluoromethyl, difluoromethyl, difluoroethyl, trifluoromethyl, hydroxymethyl, alkoxy($C_1$-$C_{18}$)methyl, phenoxymethyl, alkyl($C_1$-$C_3$)aminomethyl, dialkyl($C_1$-$C_3$)aminomethyl, aryl, substituted aryl, heteroaryl or substituted heteroaryl containing at least one —O—, —N—, or —S—, with the proviso that when $R_4$ is hydrogen, alkyl($C_1$-$C_3$), aryl or substituted aryl, $R_5$ must be fluoro; $R_5$ is hydrogen or fluoro; A is =N—, =CH—, or =CF—; and when $R_1$ is hydrogen, the pharmacologically acceptable salts thereof.

More specifically, this invention is concerned with new compounds of the formula II:

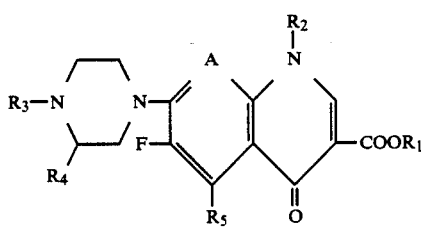

Formula II wherein $R_1$ $R_2$, $R_3$, $R_5$ and A are as described above and $R_4$ is selected from the group consisting of fluoromethyl, difluoromelthyl, trifluoromelthyl, hydroxymethyl, ethenyl, ethynyl, alkoxy($C_1$-$C^{18}$)methyl, phenoxymethyl, alkyl($C_1$-$C_3$)aminomethyl, cycloalkyl($C_3$-$C_6$), dialkyl($C_1$-$C_3$)aminomethyl, aryl, substituted aryl, heteroaryl or substituted heteroaryl containing at least one —O—, —N—, or —S—.

In addition this invention is concerned with new compounds of the formula III:

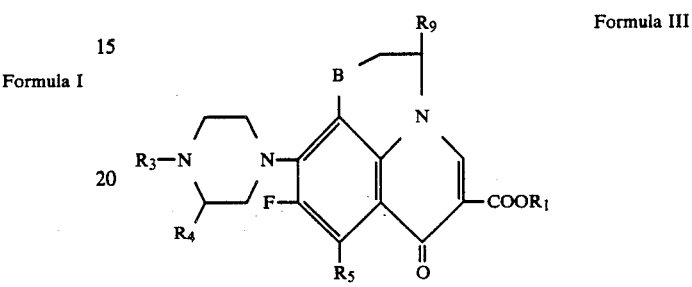

Formula III wherein $R_1$, $R_3$, $R_4$ and $R_5$ are as described for formula I; B is —O—, —S—, or —$CH_2$—; and $R_9$ is hydrogen or alkyl($C_1$-$C_3$).

Furthermore this invention is concerned with novel piperazine derivatives which are useful for the preparation of certain of the compounds of formulae I, II and III above, having the formula:

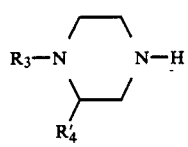

where $R_3$ is hydrogen, alkyl($C_1$-$C_3$) or benzyl; and $R_4'$ is selected from the group consisting of fluoromethyl, difluoromethyl, trifluoromethyl, alkoxy($C_1$-$C_{18}$)methyl, phenoxymethyl, alkyl($C_1$-$C_3$)aminomethyl, dialkyl($C_1$-$C_3$)aminomethyl, ethenyl, ethynyl, cycloalkyl($C_3$-$C_6$), heteroaryl or substituted heteroaryl containing at least one —O—, —N—, or —S—.

Furthermore this invention is concerned with novel compounds of the formula:

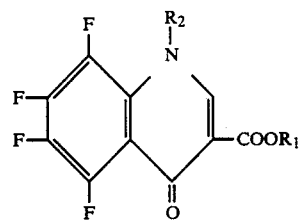

wherein $R_1$ and $R_2$ are as defined for Formula I.

DESCRIPTION OF THE INVENTION

The compounds of the present invention may be prepared according to the following reaction schemes.

Scheme A
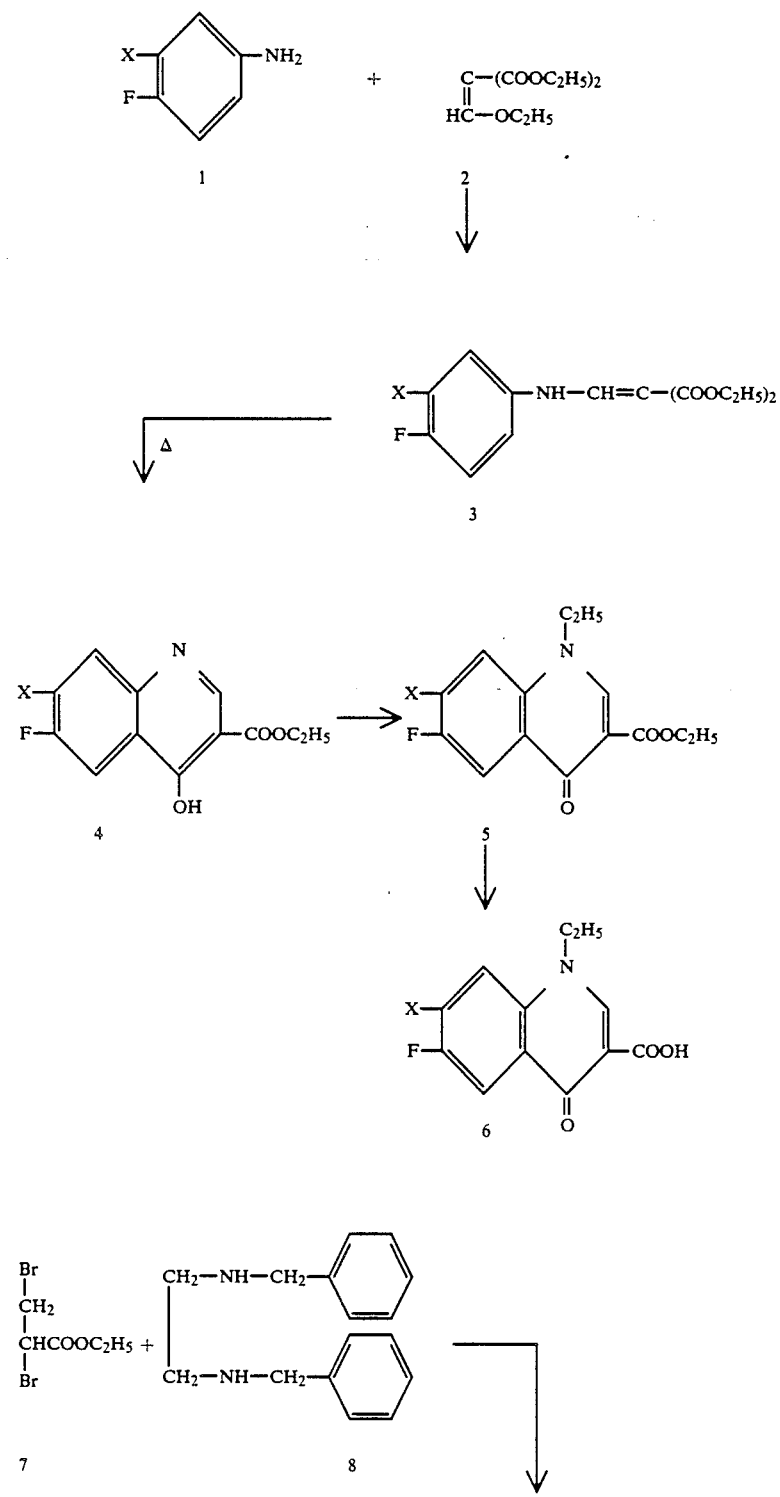

Scheme A

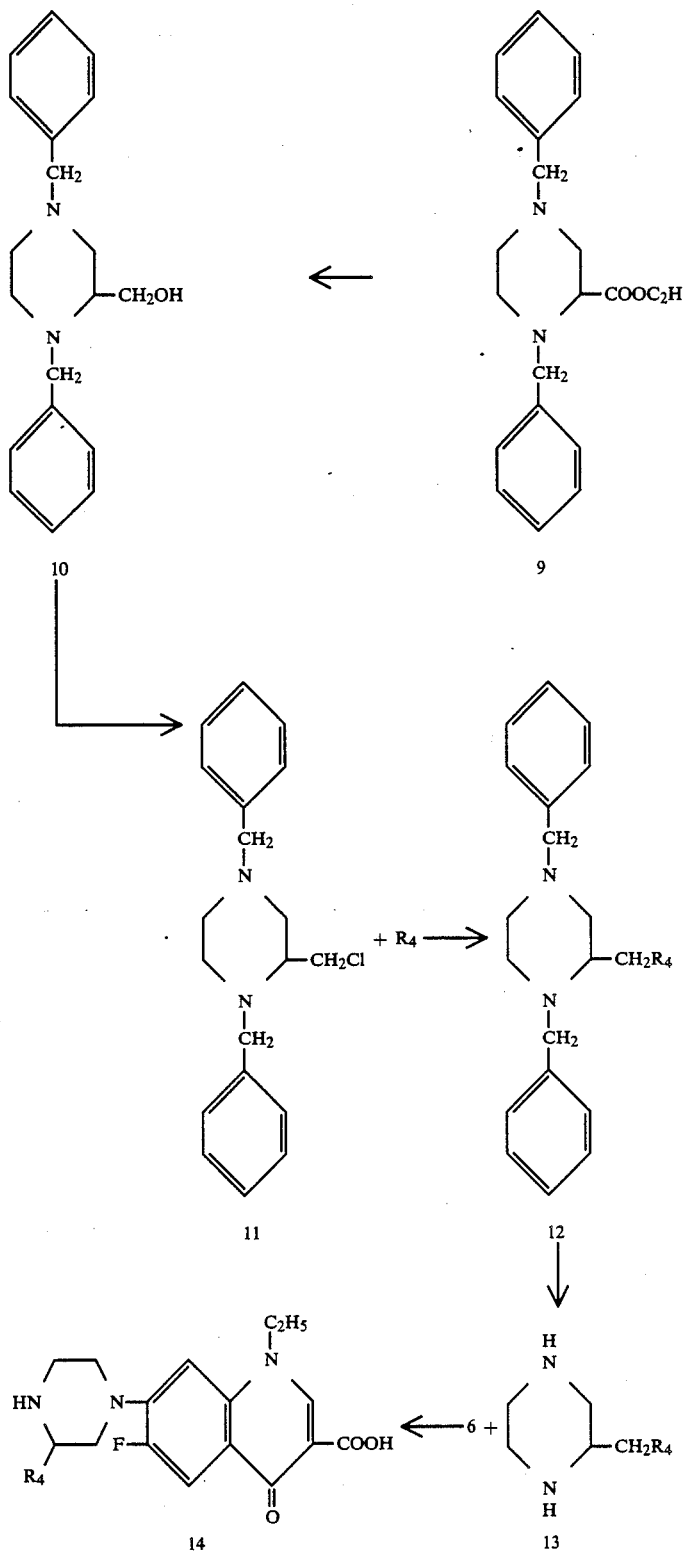

According to Scheme A, a substituted 4-fluoroaniline 1, where X is chloro or fluoro is reacted with diethyl ethoxymethylene malonate 2, with heat in vacuo, giving the aniline ester 3 which is then heated at 250°–275° C. producing 7-substituted-6-fluoro-4-hydroxy-3-quinolinecarboxylic acid, ethyl ester 4. The ester 4 is then reacted with potassium carbonate and ethyl iodide in dimethyl formamide at 80°–90° C., giving 7-substituted-1-ethyl-6-fluoro-1,4-dihydro-4-oxo-3-quinolinecarboxylic acid, ethyl ester 5 which is then refluxed in an alkali base followed by acidification giving 7-substituted-1-ethyl-6-fluoro1,4-dihydro-4-oxo-3-quinolinecarboxylic acid 6.

2,3-Dibromopropionic acid, ethyl ester 7, N,N-dibenzylethylenediamine 8 and triethylamine are reacted in toluene at 80°-100° C., giving 1,4-bis(phenylmethyl)-2-piperazinecarboxylic acid, ethyl ester 9. The ester 9 is then reacted with lithium aluminum hydride in ether, under an inert atmosphere at reflux followed by treatment with an alkali base and an alkali carbonate giving 1,4-bis(phenylmethyl)-2-piperazinemethanol 10, which is then reacted with thionyl chloride in carbon tetrachloride at 50°-60° C. followed by treatment with an alkali hydroxide, giving 2-chloromethyl-1,4-bis(phenylmethyl)piperazine 11. The compound 11 is then reacted with an amine $R_4$, where $R_4$ is dimethylamine, N-methylpiperazine, etc., giving a 2-substituted methyl-1,4-bis(phenylmethyl)piperazine 12 which is then catalytically reduced in ethanol and cyclohexane, giving piperazine derivative 13. Derivative 13 is then reacted with 6 in pyridine in a sealed unit under argon at 120°-130° C., giving 14.

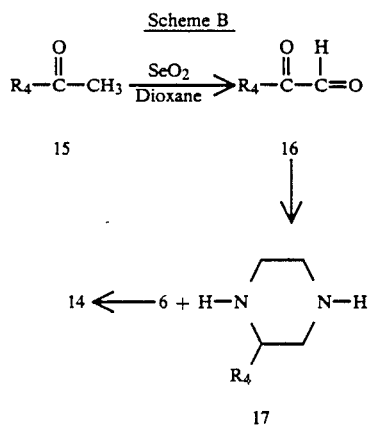

According to Scheme B, a 2-acetyl derivative 15, where $R_4$ is as described above is reacted with selenium dioxide in dioxane at reflux, giving the corresponding aldehyde 16, which is then reacted with ethylene diamine in ethanol at 0°-5° C., followed by reaction with sodium borohydride giving piperazine derivative 17. Piperazine 17 is then reacted with 7-substituted-1-ethyl-6-fluoro-1,4-dihydro-4-oxo-3-quinolinecarboxylic acid 6 as described in Scheme A, giving product 14.

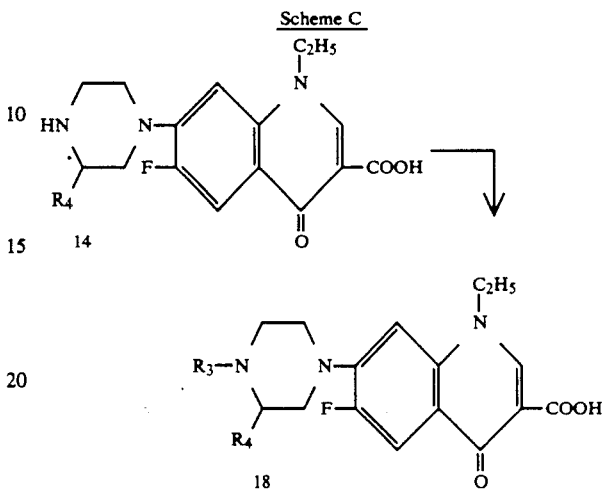

According to Scheme C a 1-ethyl-6-fluoro-1,4-dihydro-4-oxo-7-substituted-1-piperazinyl-3-quinolinecarboxylic acid 14, where $R_4$ is as described above is reacted with formalin and formic acid at reflux, giving products 18, where $R_3$ is methyl.

The compounds of the present invention are active antibacterial agents as established in the following in vitro and in vivo tests. As such they are effective in treating bacterial infections in warm-blooded animals.

The in vitro antimicrobial spectrum of the compounds of this invention were determined by the agar plate dilution method with Mueller-Hinton agar and an inoculum of each test organism of approximately $10^4$ colony forming units delivered by the Steers replicating device. The minimal inhibitory concentration (MIC) in mcg/ml is defined as the lowest concentration of test compound that inhibited visible growth after 18 hours incubation at 35° C. Results are given in Table I, with the test compounds identified by the number of their hereinafter described examples.

TABLE I

In vitro Antibacterial Spectrum

Compounds Listed by Example No.
MIC (mcg/ml)

| Organism and No. | 2 | 4 | 5 | 7 | 9 | 10 | 11 | 13 | 14 | 16 | 18 | 20 | 22 | 24 | 25 | 26 | 28 |
|---|---|---|---|---|---|---|---|---|---|---|---|---|---|---|---|---|---|
| *Escherichia coli* ATCC 25922 | 2 | 8 | 2 | 0.5 | 0.5 | 2 | 4 | 16 | >256 | 8 | 16 | >256 | >256 | ≦0.12 | 0.25 | 1 | ≦0.12 |
| *Escherichia coli* CMC 84-11 | 2 | 8 | 1 | 0.25 | 0.5 | 1 | 2 | 16 | >256 | 4 | 16 | >256 | >256 | ≦0.12 | 0.5 | 0.5 | ≦0.12 |
| *Escherichia coli* CMC 84-16 | NT | NT | NT | NT | NT | NT | NT | NT | NT | NT | NT | NT | NT | NT | NT | NT | ≦0.12 |
| *Klebsiella pneumoniae* AD | 2 | 8 | 0.5 | 0.25 | 0.5 | 1 | 4 | 16 | 256 | 4 | 16 | >256 | >256 | ≦0.12 | 0.5 | 1 | ≦0.12 |
| *Klebsiella pneumoniae* MOR 84-4 | 4 | 16 | 2 | 0.5 | 0.5 | 2 | 8 | 64 | >256 | 8 | 32 | >256 | >256 | ≦0.12 | 1 | 1 | 0.25 |
| *Klebsiella oxytoca* MOR 84-28 | NT | NT | NT | NT | NT | NT | NT | NT | NT | NT | NT | NT | NT | NT | NT | NT | 0.5 |
| *Enterobacter cloacae* VGH 84-37 | 1 | 4 | 1 | 0.25 | 0.25 | 1 | 4 | 32 | >256 | 8 | 16 | >256 | >256 | ≦0.12 | 1 | 0.5 | ≦0.12 |
| *Enterobacter cloacae* K 84-10 | NT | NT | NT | NT | NT | NT | NT | NT | NT | NT | NT | NT | NT | NT | NT | NT | 0.25 |
| *Enterobacter aerogenes* VGH 84-36 | 4 | 16 | 16 | 0.5 | 1 | 2 | 8 | >256 | >256 | 8 | 128 | >256 | >256 | ≦0.12 | 2 | 2 | 0.5 |
| *Serratia marcescens* K 84-18 | NT | NT | NT | NT | NT | NT | NT | NT | NT | NT | NT | NT | >256 | NT | NT | NT | 1 |
| *Serratia marcescens* F 0-35 | NT | NT | NT | NT | NT | NT | NT | NT | NT | NT | NT | NT | >256 | NT | NT | NT | 1 |
| *Proteus rettgeri* CMC 84-41 | 2 | 32 | 1 | 0.5 | 0.5 | 0.5 | 2 | 16 | 128 | 8 | 16 | >256 | 256 | ≦0.12 | 1 | 1 | 0.25 |
| *Morganella morganii* VGH 84-11 | 2 | 4 | 0.5 | 0.25 | 0.5 | 2 | 4 | 16 | >256 | 4 | 16 | >256 | 256 | ≦0.12 | 1 | 0.5 | 0.25 |
| *Morganella morganii* CMC 84-37 | NT | NT | NT | NT | NT | NT | NT | NT | NT | NT | NT | NT | 256 | NT | NT | NT | 0.25 |
| *Pseudomonas aeruginosa* LL-1244 | NT | NT | NT | NT | NT | NT | NT | NT | NT | NT | NT | NT | >256 | NT | NT | NT | 32 |
| *Pseudomonas aeruginosa* VGH 84-4 | 16 | 64 | 8 | 8 | 8 | 32 | 64 | >256 | >256 | >256 | >256 | >256 | >256 | 2 | 2 | 16 | 4 |
| *Acinetobacter calcoaceticus* MOR 84-43 | NT | NT | NT | NT | NT | NT | NT | NT | NT | NT | NT | NT | NT | NT | NT | NT | 2 |
| *Staphylococcus aureus* ATTC 29213 | NT | NT | NT | NT | NT | NT | NT | NT | NT | NT | NT | NT | 4 | NT | NT | NT | 0.25 |
| *Staphylococcus aureus* Smith | 0.5 | 8 | 8 | 0.5 | ≦0.12 | 1 | 1 | 0.5 | 0.25 | 0.5 | ≦0.12 | >256 | 2 | ≦0.12 | 0.5 | 0.25 | ≦0.12 |
| *Staphylococcus aureus* CMC 83-127 | NT | NT | NT | NT | NT | NT | NT | NT | NT | NT | NT | NT | 2 | NT | NT | NT | ≦0.06 |
| *Staphylococcus aureus* VGH 84-45 | NT | NT | NT | NT | NT | NT | NT | NT | NT | NT | NT | NT | 0.5 | NT | NT | NT | ≦0.06 |
| *Staphylococcus epidermidis* CMC 83-128 | NT | NT | NT | NT | NT | NT | NT | NT | NT | NT | NT | NT | 4 | NT | NT | NT | ≦0.12 |
| *Staphylococcus epidermidis* CMC 83-135 | NT | NT | NT | NT | NT | NT | NT | NT | NT | NT | NT | NT | 2 | NT | NT | NT | ≦0.12 |
| *Staphylococcus epidermidis* IO 83-58 | NT | NT | NT | NT | NT | NT | NT | NT | NT | NT | NT | NT | 8 | NT | NT | NT | 0.25 |
| *Staphylococcus* Spp saprophiticus VGH 84-50 | NT | NT | NT | NT | NT | NT | NT | NT | NT | NT | NT | NT | 32 | NT | NT | NT | 1 |
| *Streptococcus faecalis* VGH 84-65 | NT | NT | NT | NT | NT | NT | NT | NT | NT | NT | NT | NT | 256 | NT | NT | NT | 2 |
| *Escherichia coli* PRNT 311 | NT | NT | NT | NT | NT | NT | NT | NT | NT | NT | NT | NT | >256 | NT | NT | NT | 0.5 |
| *Escherichia coli* NAR 311 | NT | NT | NT | NT | NT | NT | NT | NT | NT | NT | NT | NT | >256 | NT | NT | NT | 4 |
| *Streptococcus faecalis* ATTC 29212 | NT | NT | NT | NT | NT | NT | NT | NT | NT | NT | NT | >256 | 256 | 2 | 8 | NT | 2 |
| *Staphylococcus epidermidis* VGH 84-40 | NT | NT | NT | NT | NT | NT | NT | NT | NT | NT | NT | NT | 0.5 | NT | NT | NT | ≦0.12 |

TABLE I-continued
In vitro Antibacterial Spectrum

| Organism and No. | | | | | | | | | | | | | | | | | |
|---|---|---|---|---|---|---|---|---|---|---|---|---|---|---|---|---|---|
| Staphylococcus aureus VGH 84-46 | NT | NT | NT | NT | NT | NT | NT | NT | NT | NT | NT | NT | NT | NT | NT | NT | ≦0.12 |
| Staphylococcus aureus ATCC 25913 | 2 | 64 | 32 | 2 | 0.5 | 2 | 2 | 2 | 0.5 | 1 | 2 | >256 | 2 | 4 | ≦0.12 | 0.5 | ≦0.12 |

Compounds Listed by Example No. MIC (mcg/ml)

| Organism and No. | 30 | 31 | 32 | 34 | 35 | 37 | 38 | 40 | 42 | 44 | 46 | 48 | 49 | 51 | 53 |
|---|---|---|---|---|---|---|---|---|---|---|---|---|---|---|---|
| Escherichia coli ATCC 25922 | 0.12 | 4 | 1 | 1 | 2 | 1 | 4 | 0.5 | 0.25 | 2 | 0.25 | 1 | 32 | 8 | 16 |
| Escherichia coli CMC 84-11 | 0.12 | 4 | 1 | 1 | 1 | 1 | 4 | 0.25 | ≦0.12 | 4 | 0.25 | 1 | 64 | 8 | 8 |
| Escherichia coli CMC 84-16 | 0.25 | NT | NT | NT | NT | 0.5 | NT | NT | NT | NT | NT | NT | NT | NT | 4 |
| Klebsiella pneumoniae AD | 0.12 | 4 | 2 | 1 | 2 | 2 | 4 | 0.5 | ≦0.12 | 4 | 0.5 | 1 | 64 | 8 | 64 |
| Klebsiella pneumoniae MOR 84-4 | 0.25 | 8 | 2 | 2 | 4 | 2 | 8 | 0.5 | 0.25 | 8 | 1 | 2 | 256 | 16 | 32 |
| Klebsiella oxytoca MOR 84-28 | 0.5 | NT | NT | NT | NT | 1 | NT | NT | NT | NT | NT | NT | NT | NT | >128 |
| Enterobacter cloacae VGH 84-37 | 0.12 | 4 | 1 | 1 | 2 | 1 | 8 | 0.5 | 0.25 | 4 | 0.5 | 2 | 256 | 16 | 32 |
| Enterobacter cloacae K 84-10 | 0.5 | NT | NT | NT | NT | 1 | NT | NT | NT | NT | NT | NT | NT | NT | 8 |
| Enterobacter aerogenes VGH 84-36 | 0.5 | 16 | 4 | 4 | 4 | 1 | 4 | 0.5 | 0.5 | 16 | 1 | 2 | 256 | 64 | 16 |
| Serratia marcescens K 84-18 | 0.5 | NT | NT | NT | NT | 2 | NT | NT | NT | NT | NT | NT | NT | NT | 128 |
| Serratia marcescens F 0-35 | 1 | NT | NT | NT | NT | 2 | NT | NT | NT | NT | NT | NT | NT | NT | 64 |
| Proteus rettgeri CMC 84-41 | 0.25 | 8 | 2 | 1 | 2 | 1 | 4 | 0.5 | 0.25 | 4 | 0.5 | 2 | 256 | 8 | 32 |
| Morganella morganii VGH 84-11 | 0.12 | 8 | 2 | 2 | 2 | 2 | 8 | 0.5 | 0.25 | 8 | 0.5 | 2 | 256 | 8 | 32 |
| Morganella morganii CMC 84-37 | 0.25 | NT | NT | NT | NT | 0.5 | NT | NT | NT | NT | NT | NT | NT | NT | 32 |
| Pseudomonas aeruginosa LL-1244 | 32 | NT | NT | NT | NT | 64 | NT | NT | NT | NT | NT | NT | NT | NT | >128 |
| Pseudomonas aeruginosa VGH 84-4 | 4 | 32 | 16 | 16 | 32 | 16 | >256 | 8 | 4 | >256 | 8 | 32 | >256 | >256 | >128 |
| Acinetobacter calcoaceticus MOR 84-43 | 4 | NT | NT | NT | NT | 8 | NT | NT | NT | NT | NT | NT | NT | NT | >128 |
| Staphylococcus aureus ATTC 29213 | 0.5 | NT | NT | NT | NT | 0.5 | NT | NT | NT | NT | NT | NT | NT | NT | 16 |
| Staphylococcus aureus Smith | 0.12 | 0.25 | 0.25 | 0.25 | ≦0.12 | 0.5 | 0.25 | ≦0.12 | ≦0.12 | 0.25 | ≦0.12 | 0.25 | 0.5 | 0.5 | 1 |
| Staphylococcus aureus VGH 84-45 | 0.25 | NT | NT | NT | NT | 0.12 | NT | NT | NT | NT | NT | NT | NT | NT | 16 |
| Staphylococcus aureus CMC 83-127 | 0.12 | NT | NT | NT | NT | 0.12 | NT | NT | NT | NT | NT | NT | NT | NT | 1 |
| Staphylococcus aureus CMC 83-128 | 0.5 | NT | NT | NT | NT | 0.25 | NT | NT | NT | NT | NT | NT | NT | NT | 2 |
| Staphylococcus epidermidis CMC 83-135 | 0.25 | NT | NT | NT | NT | 0.5 | NT | NT | NT | NT | NT | NT | NT | NT | 2 |
| Staphylococcus epidermidis IO 83-58 | 0.5 | NT | NT | NT | NT | 0.5 | NT | NT | NT | NT | NT | NT | NT | NT | 4 |
| Staphylococcus Spp saprophiticus VGH 84-50 | 2 | NT | NT | NT | NT | 2 | NT | NT | NT | NT | NT | NT | NT | NT | 4 |
| Streptococcus faecalis VGH 84-65 | 4 | NT | NT | NT | NT | 4 | NT | NT | NT | NT | NT | NT | NT | NT | 32 |
| Escherichia coli PRNT 311 | 0.5 | NT | NT | NT | NT | 2 | NT | NT | NT | NT | NT | NT | NT | NT | 16 |
| Escherichia coli NAR 311 | 4 | NT | NT | NT | NT | 16 | NT | NT | NT | NT | NT | NT | NT | NT | >128 |

TABLE I-continued
In vitro Antibacterial Spectrum

| Organism and No. | 4 | | | | | | | | | | | | | | | | | | | | | | |
|---|---|---|---|---|---|---|---|---|---|---|---|---|---|---|---|---|---|---|---|---|---|---|---|
| Streptococcus faecalis ATTC 29212 | 4 | NT | NT | NT | NT | NT | 4 | NT | NT | NT | NT | NT | NT | NT | 4 | 1 | 0.25 | 64 | NT | 32 | 32 |
| Staphylococcus epidermidis VGH 84-40 | 0.25 | NT | NT | NT | NT | NT | 0.25 | NT | NT | NT | NT | NT | NT | NT | NT | NT | NT | NT | NT | NT | 4 |
| Staphylococcus aureus VGH 84-46 | 0.25 | NT | NT | NT | NT | NT | 0.5 | NT | NT | NT | NT | NT | NT | NT | NT | NT | NT | 1 | NT | NT | 8 |
| Staphylococcus aureus ATCC 25913 | 0.25 | 1 | 1 | NT | NT | NT | NT | 0.25 | 0.25 | 0.25 | ≦0.12 | ≦0.12 | NT | 0.5 | ≦0.12 | 0.25 | 1 | 1 | NT |

| Organism and No. | 54 | 55 | 60 | 61 | 62 | 63 | 64 | 65 | 66 | 67 | 74 | 75 | 77 | 78 | 85 | 89 |
|---|---|---|---|---|---|---|---|---|---|---|---|---|---|---|---|---|
| Compounds Listed by Example No. MIC (mcg/ml) | | | | | | | | | | | | | | | | |
| Escherichia coli ATCC 25922 | >256 | >256 | <0.12 | <0.015 | 0.03 | 0.06 | 0.03 | 0.06 | 0.12 | 0.12 | >256 | >256 | 2 | 32 | 0.12 | 1 |
| Escherichia coli CMC 84-11 | >256 | >256 | <0.12 | 0.03 | 0.03 | 0.06 | 0.03 | 0.06 | 0.12 | 0.12 | >256 | >256 | 2 | 32 | 0.12 | 1 |
| Escherichia coli CMC 84-16 | >256 | >256 | <0.12 | <0.015 | 0.03 | 0.06 | 0.03 | 0.06 | 0.06 | 0.12 | >256 | >256 | 2 | 32 | 0.06 | 2 |
| Klebsiella pneumoniae AD | >256 | >256 | <0.12 | 0.06 | 0.12 | 0.12 | 0.06 | 0.12 | 0.25 | 0.25 | >256 | >256 | 4 | 64 | 0.25 | 2 |
| Klebsiella pneumoniae MOR 84-4 | >256 | >256 | <0.12 | 0.06 | 0.12 | 0.12 | 0.06 | 0.12 | 0.5 | 0.5 | >256 | >256 | 4 | 64 | 0.5 | 4 |
| Klebsiella oxytoca MOR 84-28 | >256 | >256 | <0.12 | 0.06 | 0.06 | NT | NT | NT | 0.12 | 0.12 | >256 | >256 | 8 | 64 | 1 | 2 |
| Enterobacter cloacae VGH 84-37 | >256 | >256 | <0.12 | 0.03 | 0.03 | 0.5 | 0.06 | 0.12 | 0.25 | 0.25 | >256 | >256 | 4 | 64 | 0.12 | 4 |
| Enterobacter cloacae K 84-10 | >256 | >256 | <0.12 | 0.03 | 0.03 | 0.12 | 0.06 | 0.06 | 0.12 | 0.12 | >256 | >256 | 4 | 64 | 0.12 | 2 |
| Enterobacter aerogenes VGH 84-36 | >256 | >256 | <0.12 | 0.03 | 0.12 | 0.25 | 0.12 | 0.12 | 2 | 1 | >256 | >256 | 4 | 64 | 0.5 | 8 |
| Serratia marcescens K 84-18 | >256 | >256 | <0.12 | 0.06 | 0.25 | 0.06 | 0.25 | 0.25 | 2 | 1 | >256 | >256 | 16 | >256 | 0.5 | 2 |
| Serratia marcescens F 0-35 | >256 | >256 | <0.12 | 0.12 | 0.06 | 0.5 | 0.5 | 0.25 | 2 | 2 | >256 | >256 | 8 | >256 | 0.5 | 2 |
| Proteus rettgeri CMC 84-41 | >256 | >256 | <0.12 | 0.12 | 0.06 | 0.5 | 0.25 | 0.25 | 1 | 1 | >256 | >256 | 8 | 64 | 0.5 | 4 |
| Morganella morganii MOR 84-4 | >256 | >256 | <0.12 | 0.06 | 0.06 | 0.5 | 0.12 | 0.12 | 1 | 1 | >256 | >256 | 4 | 32 | 0.12 | 2 |
| Morganella morganii VGH 84-11 | >256 | >256 | <0.12 | 0.06 | 0.06 | 0.12 | 0.06 | 0.12 | 0.5 | 1 | >256 | >256 | 4 | 32 | 0.12 | 4 |
| Pseudomonas aeruginosa CMC 84-37 | >256 | >256 | 4 | 4 | 4 | 8 | 8 | 8 | 16 | 4 | >256 | >256 | >256 | >256 | 16 | 64 |
| Pseudomonas aeruginosa LL-1244 | >256 | >256 | 0.5 | 0.5 | 1 | 2 | 2 | 1 | NT | NT | >256 | >256 | 128 | >256 | 4 | 32 |
| Acinetobacter calcoaceticus VGH 84-4 | >256 | >256 | NT | NT | 0.06 | 0.5 | 0.5 | 0.5 | 8 | 8 | 128 | NT | NT | NT | 1 | 2 |
| Staphylococcus aureus MOR 84-43 | 256 | 64 | <0.12 | 0.5 | 0.015 | 0.25 | 0.25 | 0.25 | 0.25 | 0.25 | 128 | >256 | 1 | 4 | 2 | 0.5 |
| Staphylococcus aureus ATCC 29213 | 64 | 16 | <0.12 | 0.25 | 0.015 | 0.25 | 0.12 | 0.25 | 0.06 | 0.03 | 128 | >256 | 2 | 8 | 1 | 0.25 |
| Staphylococcus aureus Smith | 256 | 16 | <0.12 | 0.12 | 0.015 | 0.25 | 0.12 | 0.12 | 0.03 | 0.03 | 128 | >256 | 0.5 | 8 | 1 | 0.25 |
| Staphylococcus aureus VGH 84-45 | 32 | 8 | <0.12 | 0.12 | 0.008 | 0.12 | 0.06 | 0.12 | 0.03 | 0.03 | 32 | >256 | 0.25 | 1 | 0.05 | 0.05 |
| Staphylococcus aureus CMC 83-127 | 64 | 16 | <0.12 | 0.5 | 0.03 | 0.03 | 0.25 | 0.25 | 0.06 | 0.06 | 128 | >256 | 0.5 | 4 | 2 | 1 |
| Staphylococcus aureus CMC 83-128 | 64 | 64 | <0.12 | 0.25 | 0.03 | 0.5 | 0.25 | 0.25 | NT | NT | 128 | >256 | 1 | 4 | 2 | 0.5 |
| Staphylococcus epidermidis CMC 83-135 | >256 | 128 | <0.12 | 0.25 | 0.015 | 0.25 | 0.25 | 0.25 | 8 | 0.06 | 128 | >256 | 1 | 8 | 1 | 0.5 |
| Staphylococcus epidermidis IO 83-58 | >256 | >256 | <0.12 | 2 | 0.12 | 0.06 | 1 | 1 | 0.06 | 0.25 | 64 | >256 | 2 | 8 | 8 | 4 |
| Staphylococcus Spp saprophiticus VGH 84-50 | | | | | | | | | | | | | | | | |

TABLE I-continued
In vitro Antibacterial Spectrum

| Organism and No. | 62 | 92 | 94 | 96 | 98 | 99 | 109 | 110 | 111 | 119 | 121 | 122 | 123 | 124 | 125 | 127 | 128 | 129 |
|---|---|---|---|---|---|---|---|---|---|---|---|---|---|---|---|---|---|---|
| Streptococcus faecalis VGH 84-65 | >256 | >256 | <0.12 | | 2 | 0.5 | 4 | 4 | 4 | 0.25 | 1 | 128 | | | 8 | 16 | 16 | 32 |
| Escherichia coli PRNT 311 | >256 | >256 | <0.12 | | 0.03 | 0.06 | >16 | 4 | 0.06 | 0.5 | 0.5 | 0.25 | >256 | | 2 | 16 | 0.12 | 2 |
| Escherichia coli NAR 311 | >256 | >256 | 0.25 | | 0.5 | 0.5 | >16 | 4 | 1 | 0.5 | 2 | 2 | >256 | | 32 | 256 | 4 | 128 |
| Streptococcus faecalis ATTC 29212 | >256 | >256 | <0.12 | | 2 | 0.25 | >16 | 8 | 4 | 0.5 | 0.5 | 4 | >256 | | 8 | 16 | 8 | 8 |
| Staphylococcus epidermidis VGH 84-40 | >256 | 32 | <0.12 | | 0.25 | 0.03 | >16 | 16 | 0.015 | 0.06 | 0.06 | 64 | >256 | | 0.25 | 2 | 1 | NT |
| Staphylococcus aureus VGH 84-46 | >256 | 32 | <0.12 | | 0.25 | 0.015 | >16 | 16 | 0.004 | 0.12 | 0.06 | 0.06 | >256 | | 0.5 | 4 | 1 | NT |
| Staphylococcus aureus ATCC 25913 | NT | NT | NT | | NT | NT | NT | NT | NT | NT | NT | NT | NT | | NT | NT | NT | NT |

Compounds Listed by Example No.
MIC (mcg/ml)

| Organism and No. | 62 | 92 | 94 | 96 | 98 | 99 | 109 | 110 | 111 | 119 | 121 | 122 | 123 | 124 | 125 | 127 | 128 | 129 |
|---|---|---|---|---|---|---|---|---|---|---|---|---|---|---|---|---|---|---|
| Escherichia coli MOR 84-20 | 0.06 | 0.06 | 0.25 | 0.008 | 0.12 | 0.06 | >16 | 4 | 0.004 | 0.015 | 0.25 | 1 | 2 | 0.015 | 0.25 | 1 | 0.25 | 0.12 |
| Escherichia coli VGH 84-19 | 0.06 | 0.06 | 0.25 | 0.008 | 0.12 | 0.06 | >16 | 4 | 0.004 | 0.015 | 0.25 | 1 | 2 | 0.015 | 0.25 | 1 | 0.25 | 0.12 |
| Escherichia coli CMC 84-50 | 0.12 | 0.12 | 0.25 | 0.015 | 0.12 | 0.12 | >16 | 4 | 0.004 | 0.03 | 0.25 | 2 | 4 | 0.03 | 0.25 | 2 | 0.5 | 0.25 |
| Klebsiella pneumoniae CMC 84-31 | 0.12 | 0.12 | 0.5 | 0.015 | 0.12 | 0.12 | >16 | 8 | 0.015 | 0.06 | 0.25 | 4 | 4 | 0.03 | 0.25 | 2 | 0.5 | 0.25 |
| Klebsiella pneumoniae MOR 84-24 | 0.25 | 0.25 | 1 | 0.03 | 0.25 | 0.25 | >16 | 16 | 0.06 | 0.12 | 1 | 4 | 8 | 0.06 | 0.5 | 4 | 1 | 0.5 |
| Klebsiella pneumoniae IO 83-5 | 0.25 | 0.12 | 1 | 0.03 | 0.25 | 0.015 | >16 | 16 | 0.06 | 0.12 | 1 | 2 | 8 | 0.06 | 0.5 | 4 | 1 | 0.5 |
| Enterobacter cloacae VGH 84-39 | 0.12 | 0.12 | 0.5 | 0.015 | 0.12 | 0.12 | >16 | 8 | 0.004 | 0.06 | 0.5 | 2 | 4 | 0.03 | 0.5 | 2 | 0.5 | 0.25 |
| Enterobacter cloacae K 84-10 | 0.12 | 0.06 | 0.25 | 0.015 | 0.06 | 0.06 | 16 | 4 | 0.004 | 0.03 | 0.25 | 1 | 2 | 0.015 | 0.06 | 2 | 0.12 | 0.12 |
| Enterobacter cloacae MOR 84-30 | 1 | 1 | 4 | 0.25 | 1 | 0.25 | >16 | >16 | 0.06 | 0.5 | 4 | 16 | >16 | 0.5 | 2 | 8 | 1 | 0.5 |
| Serratia marcescens MOR 84-41 | 0.5 | 0.25 | 0.5 | 0.06 | 0.25 | 0.25 | >16 | >16 | 0.06 | 0.5 | 1 | 4 | 8 | 0.12 | 1 | 4 | 1 | 0.5 |
| Serratia marcescens IO 83-63 | 16 | 8 | 16 | 4 | 8 | 8 | >16 | >16 | 4 | 16 | >16 | >16 | >16 | 8 | >16 | >16 | >16 | 16 |
| Serratia marcescens CMC 83-74 | 1 | 1 | 1 | 0.25 | 1 | 1 | >16 | >16 | 0.25 | 2 | 8 | 16 | 8 | 0.5 | 4 | 8 | 4 | 2 |
| Morganella morganii VHG 84-12 | 0.5 | 0.25 | 1 | 0.12 | 0.25 | 0.5 | >16 | >16 | 0.06 | 0.5 | 4 | 8 | 8 | 0.12 | 1 | 4 | 1 | 0.5 |
| Morganella morganii CMC 84-38 | 0.25 | 0.25 | 0.25 | 0.03 | 0.12 | 0.12 | >16 | 8 | 0.008 | 0.06 | 0.5 | 1 | 2 | 0.03 | 0.5 | 2 | 0.5 | 0.25 |
| Morganella morganii MOR 84-45 | 0.12 | 0.12 | 0.12 | 0.008 | 0.12 | 0.12 | >16 | 8 | 0.004 | 0.03 | 0.25 | 1 | 2 | 0.015 | 0.5 | 2 | 0.5 | 0.25 |
| Proteus rettgeri IO 83-21 | 0.25 | 0.5 | 1 | 0.12 | 0.5 | 0.25 | >16 | 16 | 0.008 | 0.12 | 1 | 4 | 8 | 0.12 | 1 | 4 | 1 | 0.5 |
| Providencia stuarti CMC 83-3 | 16 | 8 | 16 | 2 | 8 | 8 | >16 | >16 | 8 | 4 | >16 | >16 | >16 | 4 | >16 | >16 | >16 | 16 |
| Citrobacter div. K 82-24 | 0.12 | 0.06 | 0.25 | 0.008 | 0.12 | 0.12 | >16 | 8 | 0.002 | 0.03 | 0.25 | 2 | 4 | 0.03 | 0.25 | 2 | 0.25 | 0.25 |
| Pseudomonas aeruginosa K 84-16 | 8 | 4 | 16 | 2 | 4 | 4 | >16 | >16 | 4 | 4 | 4 | >16 | >16 | 4 | 16 | >16 | 16 | 16 |
| Pseudomonas aeruginosa VGH 84-3 | >16 | 16 | >16 | 4 | 16 | 16 | >16 | 16 | 8 | 8 | 8 | >16 | >16 | 8 | >16 | >16 | >16 | >16 |
| Pseudomonas aeruginosa CMC 83-20 | 8 | 4 | 8 | 1 | 4 | 4 | >16 | >16 | 4 | 2 | 16 | 1 | >16 | 4 | 16 | >16 | 16 | 16 |
| Staphylococcus aureus VGH 84-47 | 0.03 | 0.12 | 0.25 | 0.06 | 0.12 | 0.03 | 2 | 1 | 0.12 | 0.12 | 1 | 1 | 2 | 0.25 | 0.5 | 0.25 | 0.25 | 0.12 |

TABLE I-continued
In vitro Antibacterial Spectrum

| Organism and No. | | | | | | | | | | | | |
|---|---|---|---|---|---|---|---|---|---|---|---|---|
| Staphylococcus aureus K 82-26 | 0.06 | 0.12 | 0.25 | 0.12 | 0.03 | >16 | 16 | 1 | 0.5 | 1 | 1 | 2 |
| Staphylococcus aureus CMC 83-131 | 0.25 | NT | NT | 0.25 | NT | 2 | 2 | 0.25 | 0.25 | 2 | 16 | 0.25 |
| Streptococcus faecalis UCI 85-30 | 1 | 1 | 4 | 2 | 1 | >16 | >16 | 1 | 1 | 0.5 | 2 | 4 |
| Streptococcus faecalis VGH 84-69 | 0.5 | 1 | 2 | 1 | 0.5 | 0.5 | >16 | 2 | 0.5 | 2 | 1 | 2 |
| Streptococcus faecalis CMC 83-120 | 1 | 1 | 4 | 1 | 1 | >16 | 16 | 2 | 0.5 | 1 | 1 | 2 |
| Escherichia coli ATCC 25922 | 0.06 | 0.12 | 0.5 | 0.015 | 0.12 | 8 | 1 | 0.008 | 0.004 | 0.008 | 1 | 0.06 |
| Staphylococcus aureus ATCC 29213 | 0.06 | 0.12 | 1 | 0.25 | 0.03 | 1 | 1 | 0.12 | 0.25 | 0.25 | 1 | 0.25 |

Compounds Listed by Example No.
MIC (mcg/ml)

| Organism and No. | 81 | 82 | 83 | 84 | 90 | 91 | 92 | 94 | 96 | 98 | 99 | 100 | 109 |
|---|---|---|---|---|---|---|---|---|---|---|---|---|---|
| Escherichia coli LL 311 | 0.03 | 0.25 | 0.12 | 1 | 0.25 | 0.25 | 0.03 | 0.12 | 0.03 | 0.03 | 0.03 | 0.25 | 8 |
| Escherichia coli CMC 84-11 | 0.03 | 0.12 | 0.06 | 1 | 0.25 | 0.25 | 0.03 | 0.12 | <0.015 | 0.03 | 0.03 | 0.12 | 16 |
| Serratia marcescens K 84-18 | 0.5 | 2 | 0.5 | 32 | 1 | 0.5 | 0.25 | 0.5 | <0.015 | 0.25 | 0.5 | 4 | 32 |
| Serratia marcescens VGH 84-30 | 4 | 16 | 4 | >128 | 16 | 16 | 4 | 8 | 1 | 4 | 8 | 64 | >128 |
| Proteus rettgeri CMC 84-41 | 0.12 | 1 | 0.25 | 1 | 1 | 0.25 | 0.12 | 0.25 | 0.03 | 0.12 | 0.12 | 1 | 32 |
| Morganella morganii CMC 84-37 | 0.06 | 1 | 0.12 | 2 | 0.25 | 0.12 | 0.06 | 0.12 | 0.03 | 0.06 | 0.12 | 0.5 | NT |
| Pseudomonas aeruginosa LL 1244 | 8 | 32 | 32 | >128 | 32 | 8 | 2 | 8 | 1 | 2 | 4 | 16 | >128 |
| Pseudomonas aeruginosa VGH 84-4 | 2 | 8 | 4 | 32 | 16 | 8 | 2 | 4 | 1 | 2 | 2 | 8 | >128 |
| Staphylococcus aureus VGH 84-45 | 0.12 | 0.12 | 0.03 | 0.25 | 0.25 | 2 | 0.03 | 0.12 | 0.06 | 0.03 | 0.03 | 0.03 | 0.5 |
| Staphylococcus aureus Smith | 0.12 | 0.12 | 0.06 | 0.25 | 0.25 | 2 | 0.03 | 0.12 | 0.06 | 0.03 | <0.015 | 0.008 | 0.25 |
| Streptococcus faecalis VGH 84-65 | 2 | 8 | 2 | 32 | 8 | 32 | 0.5 | 2 | 0.5 | 0.5 | 0.5 | 2 | 16 |
| Streptococcus faecalis UCI 85-19 | 2 | 8 | 2 | 32 | 8 | 32 | 1 | 4 | 0.5 | 0.5 | 0.5 | 2 | 16 |
| Escherichia coli ATCC 25922 | 0.25 | 0.25 | 0.12 | 1 | 0.25 | 0.5 | 0.06 | 0.25 | 0.015 | 0.06 | 0.06 | 0.25 | 8 |
| Staphylococcus aureus ATCC 29213 | 0.25 | 0.5 | 0.25 | 1 | 1 | 4 | 0.06 | 0.25 | 0.25 | 0.06 | 0.03 | 0.06 | 0.5 |

Compounds Listed by Example No.
MIC (mcg/ml)

| Organism and No. | 110 | 111 | 113 | 114 | 115 | 116 | 117 | 121 | 122 | 123 | 124 | 125 | 127 | 128 | 129 |
|---|---|---|---|---|---|---|---|---|---|---|---|---|---|---|---|
| Escherichia coli LL 311 | 2 | 0.015 | 0.5 | 0.25 | 0.5 | 0.12 | 0.12 | 0.12 | 0.25 | 1 | 0.03 | 0.06 | 0.5 | 0.06 | 0.06 |
| Escherichia coli CMC 84-11 | 2 | 0.015 | 0.25 | 0.12 | 0.5 | 0.06 | 0.12 | 0.06 | 0.25 | 2 | 0.03 | 0.06 | 0.5 | 0.06 | 0.03 |
| Serratia marcescens K 84-18 | 8 | 0.12 | 2 | 1 | 2 | 0.5 | 0.25 | 0.25 | 1 | 8 | 0.12 | 0.5 | 1 | 0.5 | 0.25 |
| Serratia marcescens VGH 84-30 | >128 | 2 | 16 | 16 | 32 | 8 | 8 | 32 | 32 | 64 | 2 | 8 | 32 | 8 | 8 |
| Proteus rettgeri CMC 84-41 | 4 | 0.03 | 2 | 2 | 2 | 0.5 | 0.5 | 0.5 | 0.25 | 2 | 0.06 | 0.25 | 1 | 0.12 | 0.12 |
| Morganella morganii CMC 84-37 | NT | 0.03 | 1 | 1 | 1 | 0.25 | 0.25 | 1 | 0.25 | NT | 0.06 | 0.25 | 0.5 | 0.25 | 0.12 |

TABLE I-continued

In vitro Antibacterial Spectrum

| Organism | | | | | | | | | | | | | | |
|---|---|---|---|---|---|---|---|---|---|---|---|---|---|---|
| Pseudomonas aeruginosa LL 1244 | 128 | 4 | 32 | 16 | 16 | 8 | 16 | 32 | 64 | 4 | 16 | 16 | 8 | 8 |
| Pseudomonas aeruginosa VGH 84-4 | 128 | 2 | 8 | 8 | 8 | 4 | 8 | 32 | 64 | 2 | 8 | 16 | 8 | 8 |
| Staphylococcus aureus VGH 84-45 | 0.5 | 0.12 | 0.25 | 0.25 | 0.5 | 0.12 | 0.5 | 0.25 | 0.5 | 0.06 | 0.12 | 0.12 | 0.06 | 0.03 |
| Staphylococcus aureus Smith | 0.25/8 | 0.25/4 | 0.25/8 | 0.12/4 | 0.5/8 | 0.12/2 | 0.12/2 | 0.12/8 | 0.5/8 | 0.06/1 | 0.12/4 | 0.06/2 | 0.06/1 | 0.03/1 |
| Streptococcus faecalis VGH 84-65 | 8 | 4 | 8 | 4 | 8 | 2 | 2 | 4 | 8 | 2 | 4 | 4 | 2 | 2 |
| Streptococcus faecalis UCI 85-19 | 1/0.5 | <0.015/0.25 | 0.25/8 | 0.12/8 | 0.25/8 | 0.06/2 | 0.03/1 | 0.12/0.5 | 1/0.5 | <0.015/0.12 | 0.03/0.25 | 0.25/0.12 | 0.03/0.12 | 0.03/0.12 |

The in vivo antibacterial activity of the compounds of this invention were established in the following tests.

Charles River CD-1 mice were infected with either *Klebsiella pneumonia* AD or *Staphylococcus aureus* Smith. A single subcutaneous dose of the test compound was administered ½ hour after infection. The mice were observed for 7 days and survival ratios recorded. The results appear in Tables II and III, wherein the representative test compounds are identified by the number of their hereinafter described examples.

TABLE II

In vivo Results Against *Klebsiella pneumoniae* AD

| Subcutaneous Dose (mg/kg) | Survival Ratio 7 Days After Infection Example No. | | | | | |
|---|---|---|---|---|---|---|
| | 1 | 4 | 5 | 16 | 17 | 18 |
| 64 | NT | 5/5 | 5/5 | NT | NT | 5/5 |
| 16 | 5/5 | 5/5 | 0/5 | 1/5 | 5/5 | 4/5 |
| 8 | NT | NT | NT | NT | 5/5 | NT |
| 4 | 1/5 | 4/5 | 0/5 | 1/5 | 1/5 | 1/5 |
| 2 | NT | NT | NT | NT | 0/5 | NT |
| 1 | 0/5 | 0/5 | 0/5 | 0/5 | 0/5 | 0/5 |
| 0.5 | NT | NT | NT | NT | 0/5 | NT |
| 0.25 | 0/5 | 0/5 | 0/5 | 0/5 | 0/5 | 0/5 |

NT = Not tested

TABLE III

In vivo Results Against *Staphylococcus aureus* Smith

| Subcutaneous Dose (mg/kg) | Survival Ratio 7 Days After Infection Example No. | | |
|---|---|---|---|
| | 14 | 18 | 23 |
| 64 | NT | NT | 5/5 |
| 32 | NT | NT | 5/5 |
| 16 | NT | NT | 5/5 |
| 8 | 5/5 | 2/5 | 0/5 |
| 4 | 5/5 | 0/5 | 0/5 |
| 2 | 0/5 | 0/5 | NT |
| 1 | 0/5 | 0/5 | NT |
| 0.5 | 0/5 | 0/5 | NT |

NT = Not tested

The in vivo antibacterial activity of 1-cyclopropyl-6-fluoro-7-[3-(fluoromethyl)-1-piperazinyl]-1,4-dihydro-4-oxo-3-quinolinecarboxylic acid (Example 131) was established in the following test.

Charles River CD-1 female mice, weighing 20±2 g were infected with either *Staphylococcus aureus* Smith or *Escherichia coli* 311. A single oral or subcutaneous dose of 1-cyclopropyl-6-fluoro-7-[3-(fluoromethyl)-1-piperazinyl]-1,4-dihydro-4-oxo-3-quinolinecaboxylic acid was administered ½ hour after infection. The mice were observed for 7 days and survival ratios recorded. The results appear in Table IV.

TABLE IV

In vivo Results for 1-Cyclopropyl-6-fluoro-7-[3-(fluoromethyl)-1-piperazinyl]-1,4-dihydro-4-oxo-3-quinolinecarboxylic acid

| Dose (mg/kg) | Survival Ratio 7 Days After Infection | | | |
|---|---|---|---|---|
| | S. aureus Smith | | E. coli 311 | |
| | Oral | Subcutaneous | Oral | Subcutaneous |
| 8 | 15/15 | NT | NT | NT |
| 4 | 10/15 | 15/15 | NT | NT |
| 2 | 2/15 | 14/15 | 10/10 | 10/10 |
| 1 | 0/15 | 2/15 | 7/10 | 10/10 |
| 0.5 | NT | 0/15 | 3/10 | 7/10 |
| 0.25 | NT | NT | 1/10 | 2/10 |

TABLE IV-continued

In vivo Results for 1-Cyclopropyl-6-fluoro-7-[3-(fluoromethyl)-1-piperazinyl]-1,4-dihydro-4-oxo-3-quinolinecarboxylic acid

| Dose (mg/kg) | Survival Ratio 7 Days After Infection | | | |
|---|---|---|---|---|
| | S. aureus Smith | | E. coli 311 | |
| | Oral | Subcutaneous | Oral | Subcutaneous |
| 0.12 | NT | NT | 0/10 | 0/10 |

NT = Not tested.

When the compounds are employed for the above utility, they may be combined with one or more pharmaceutically acceptable carriers, for example, solvents, diluents and the like, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing, for example, from about 20 to 50% ethanol, and the like, or parenterally in the form of sterile injectable solutions or suspensions containing from about 0.05 to 5% suspending agent in an isotonic medium. Such pharmaceutical preparations may contain, for example, from about 0.05 up to about 90% of the active ingredient in combination with the carrier, more usually between about 5% and 60% by weight.

The effective dosage of active ingredient employed may vary depending on the particular compound employed, the mode of administration and the severity of the condition being treated. However, in general, satisfactory results are obtained when the compounds of the invention are administered at a daily dosage of from about 2 to about 100 mg/kg of animal body weight, preferably given in divided doses two to four times a day, or in sustained release form. For most large mammals the total daily dosage is from about 100 to about 750 mg, preferably from about 100 to 500 mg. Dosage forms suitable for internal use comprise from about 100 to 750 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation. A decided practical advantage is that these active compounds may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the stand-point of ease of preparation and administration are solid composition, particularly tablets and hardfilled or liquid-filled capsules, Oral administration of the compounds is preferred.

These active compounds may also be administered parenterally or intraperitoneally. Solutions or suspensions of these active compounds as a free base or pharmacologically acceptable salt can be prepared in-water suitably mixed with a surfactant such as hydroxypropylcellulose. Dispersions can also be prepared in glycerol, liquid polyethylene glycols, and mixtures thereof in oils. Under ordinary conditions of storage and use, these preparations contain a preservative to prevent the growth of microorganisms.

The pharmaceutical forms suitable for injection use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

The invention will be more fully described in conjunction with the following specific examples which are not to be construed as limiting the scope of the invention.

EXAMPLE 1

N,N-Dimethyl-2-piperazinemethanamine

A 29.1 g portion of 2,3-dibromopropionic acid, ethyl ester was dissolved in 90 ml of dry toluene at 40° C. in an oil bath. With vigorous stirring, a stream of a solution of 26.8 g of N,N'-dibenzylethylenediamine and 30.5 ml of triethylamine in 28 ml of dry toluene was added. The temperature was raised to 80° C. and stirring continued for 3 hours. The mixture was filtered, the solid washed with two 50 ml portions of toluene and the filtrate and washes combined. The solution was washed with three 50 ml portions of water, dried, filtered and concentrated to an oil. The oil was distilled and the fraction boiling at 185°-195° C., 0.75 mm collected, giving 1,4-bis(phenylmethyl)-2-piperazinecarboxylic acid, ethyl ester as a yellow oil.

A 3.06 g portion of lithium aluminum hydride in 130 ml of dry ether, with argon bubbling through the solution, was stirred at room temperature. A solution of 24.5 g of 1,4-bis(phenylmethyl)-2-piperazinecarboxylic acid, ethyl ester in 125 ml of dry ether was added, the mixture was heated at reflux for 5 hours and then cooled. A 40 ml portion of 40% aqueous potassium hydroxide followed by 80 ml of saturated aqueous potassium carbonate were added dropwise, under argon. The mixture was allowed to stand overnight, after stirring for one hour. The ether layer was removed and saved, then the remainder filtered. The filtrate was extracted several times with ether. The ether solutions were combined, dried, filtered and evaporated, giving 22.15 g of 1,4-bis(phenylmethyl)2-piperazinemethanol as a colorless oil.

To a solution of 10.1 ml of thionyl chloride in 50 ml of carbon tetrachloride was added, with stirring, a solution of 22.15 g of 1,4-bis(phenylmethyl)-2-piperazinemethanol in 120 ml of carbon tetrachloride. This mixture was stirred in an oil bath at 70° C. for one hour, then cooled in an ice bath and a solution of 17.1 g of potassium hydroxide in 50 ml of water was added. The mixture was extracted several times with dichloromethane. The extracts were combined, filtered through hydrous magnesium silicate and evaporated. The residual gum was dissolved in warm heptane, filtered and evaporated to an oil which crystallized on standing, giving 17.94 g of 2-chloromethyl-1,4-bis(phenylmethyl)piperazine, mp 54°-56° C.

A 6 g portion of 2-chloromethyl-1,4-bis(phenylmethyl)piperazine was dissolved in 20 ml of dioxane. To this was added 3.14 g of potassium carbonate and 68 ml of 40% aqueous dimethylamine. The mixture was stirred in a sealed pressure bottle at 80° C. for 18 hours and then taken to dryness in vacuo. The gummy residue was mixed with water and dichloromethane. The aqueous layer was washed twice with dichloromethane. The organic solutions were combined, dried, filtered and evaporated, giving 6.23 g of 2-dimethylaminomethyl-1,4-bis(phenylmethyl)piperazine as a gum.

A 4.7 g portion of 2-dimethylaminomethyl-1,4-bis(phenylmethyl)piperazine was dissolved in a mixture of 50 ml of ethanol, 20 ml of cyclohexane and 10 ml of glacial acetic acid. A 2.0 g portion of 10% palladium on carbon was added, the mixture was refluxed overnight and then filtered. The filtrate was evaporated, 5 ml of saturated aqueous potassium bicarbonate was added to the residue and this was extracted several times with dichloromethane. The extracts were combined, dried, filtered and evaporated, giving a gum which solidified on standing, giving 1.02 g of N,N-dimethyl-2-piperazinemethanamine.

EXAMPLE 2

7-[3-[(Dimethylamino)methyl]-1-piperazinyl]-1-ethyl-6-fluoro-1,4-dihydro-4-oxo-3-quinolinecarboxylic acid A 100 g portion of 3-chloro-4-fluoroaniline and 148.5 g of diethyl ethoxymethylene malonate were heated, with stirring in an oil bath at 120°-130° C. for 2 hours, under vacuum. The mixture was then evaporated in vacuo to an oil, 150 ml of hexane was added and the mixture was stirred with cooling. The resulting solid was collected, washed with cold hexane and dried in vacuo.

A 100 g portion of the above solid was stirred and heated at 250°-265° C. in an oil bath under slight vacuum. The resulting oil was maintained at 260°-265° C. for 0.5 hours until completely solidified, then cooled, triturated with dichloromethane and the solid collected, giving 59.85 g of 7-chloro-6-fluoro-4-hydroxy-3-quinolinecarboxylic acid, ethyl ester.

A 59.7 g portion of the above ester was suspended in 425 ml of dimethylformamide, 76.6 g of potassium carbonate was added and this mixture was stirred in an oil bath at 80°-90° C. An 89 ml portion of ethyl iodide was added, the mixture was stirred at 80°-90° C. for 18 hours and then evaporated. The residue was dissolved in water and then extracted with dichloromethane. The extract was washed with water, dried, filtered through hydrous magnesium silicate and evaporated in vacuo. The solid was recrystallized from ethanol, giving 38 g of 7-chloro-1-ethyl-6-fluoro-1,4-dihydro-4-oxo-3-quinolinecarboxylic acid, ethyl ester.

A 25 g portion of the above ester in 243 ml of 2N aqueous sodium hydroxide was refluxed for 2 hours, then cooled and acidified with glacial acetic acid. The mixture was refrigerated overnight and the solid collected and recrystallized from dimethylformamide, giving 17.6 g of 7-chloro-1-ethyl-6-fluoro-1,4-dihydro-4-oxo-3-quinolinecarboxylic acid as a pale yellow solid, mp 285°-286° C.

A mixture of 480 mg of 7-chloro-1-ethyl-6-fluoro-1,4-dihydro-4-oxo-3-quinolinecarboxylic acid, 1.0 g of 2-dimethylaminomethylpiperazine and 5 ml of pyridine in a sealed flask flushed with argon was stirred at 120°–130° C. for 18 hours. The solvent was removed in vacuo. The residue was evaporated twice from toluene, giving a gum. The gum was added to a silica gel column and flash chromatographed with methanol:chloroform (1.5:8.5 saturated with water). Fractions 61 and 62 were combined, evaporated and dried, giving 105 mg of the desired product as a white solid, mp 148°–150° C.

EXAMPLE 3

1-Methyl-4-(2-piperazinylmethyl)piperazine

A mixture of 7.7 g of 2-chloromethyl-1,4-bis(phenylmethyl)piperazine, 12 g of N-methylpiperazine, 3.5 g of potassium carbonate, 150 ml of dioxane and 60 ml of water was heated overnight at 80°–90° C. and then evaporated. The residual gum was dissolved in dichloromethane, washed with water, dried, filtered and evaporated, giving 8.8 g of 2-[(N-methylpiperazinyl)methyl]-1,4-bis(phenylmethyl)piperazine.

A 7.8 g portion of the above compound, 200 ml of ethanol, 80 ml of cyclohexane, 40 ml of glacial acetic acid and 3.2 g of 10% palladium on carbon were mixed and refluxed for 18 hours. The solvents were removed, heptane was added and removed. Saturated aqueous potassium carbonate was added until the reaction was basic. The mixture was then extracted with dichloromethane several times, dried, filtered and evaporated giving a gum. A 2 ml portion of 40% aqueous potassium hydroxide was added and this mixture was extracted with dichloromethane. The extract was dried, filtered and evaporated to a gum. Ether was added, the mixture was filtered and the filtrate evaporated, giving a gum which solidified, giving 1.25 g of 1-methyl-4-(2-piperazinylmethyl)piperazine.

EXAMPLE 4

1-Ethyl-6-fluoro 1,4-dihydro-7-[3-[(4-methyl-1-piperazinyl)methyl]-1-piperazinyl]-4-oxo-3-quinolinecarboxylic acid A 425 mg portion of 7-chloro-1-ethyl-6-fluoro-1,4-dihydro-4-oxo-3-quinolinecarboxylic acid and 1.25 g of 1-methyl-4-(2-piperazinylmethyl)piperazine were suspended in 5 ml of pyridine and heated at reflux, under argon, for 18 hours. The solvents were removed and the residue evaporated twice from toluene. The residue was dissolved in dichloromethane, hexane was added, the resulting gum was separated, dissolved in dichloromethane and filtered. Ether was added to the filtrate, the resulting solid collected and recyrstallized, giving 360 mg of the desired product as a yellow solid.

EXAMPLE 5

1-Ethyl-6-fluoro-1,4-dihydro-7-[3-(hydroxymethyl)-1-piperazinyl]-4-oxo-3-quinolinecarboxylic acid, hydrochloride A mixture of 2 g of 2-hydroxymethylpiperazine, 1 g of 7-chloro-1-ethyl-6-fluoro-1,4-dihydro-4-oxo-3-quinolinecarboxylic acid and 8 ml of pyridine was heated at 130° C. in a sealed bottle, under argon, overnight. The solvent was removed and the residue adsorbed onto silica gel, then added to a column of flash grade silica gel. The column was eluted with methanol:water (95:5). The product fraction was collected, dissolved in methanol:dichloromethane and converted to the hydrochloride salt, mp >275° C.

EXAMPLE 6

2-(Methoxymethyl)piperazine

To 25 ml of ether, under argon, was added 2.5 g of heptane washed, 50% sodium hydride. To this was added with stirring, a solution of 5 g of 1,4-bis(phenylmethyl)-2-piperazinemethanol in 15 ml of dimethylformamide. This mixture was stirred for one hour, then cooled to 10° C. and a solution of 1.4 ml of methyl iodide in 10 ml of ether was added dropwise. The mixture was stirred at room temperature for 2 hours and then decomposed with water, dropwise, still under argon. The mixture was extracted with ether several times, the extracts combined, washed with water, dried, filtered and evaporated, giving 5 g of 1,4-bis(phenylmethyl)-2-methoxymethylpiperazine.

A 4.8 g portion of the above compound was dissolved in 150 ml of ether and 1.2 g of 10% palladium on carbon were added. This mixture was hydrogenated at 40° C. overnight, then filtered. The filtrate was evaporated to an oil which was dissolved in dichloromethane, filtered through hydrous magnesium silicate and evaporated, giving 2-(methoxymethyl)piperazine as an oil.

EXAMPLE 7

1-Ethyl-6-fluoro-1,4-dihydro-7-[3-(methoxymethyl)-1-piperazinyl]-4-oxo-3-quinolinecarboxylic acid A 1.7 g portion of 2-(methoxymethyl)piperazine was dissolved in 8 ml of pyridine. A 0.88 g portion of 7-chloro-1-ethyl-6-fluoro-1,4-dihydro-4-oxo-3-quinolinecarboxylic acid was added and the mixture was heated in a pressure bottle, under argon, at 120°–130° C. for 18 hours. The solvents were removed and the resulting gum evaporated three times from toluene. The residue was purified by column chromatography, eluting with chloroform:methanol saturated with water (90:10). The appropriate fractions were combined and evaporated, giving 550 mg of the desired product, mp 169°–170° C.

EXAMPLE 8

3-(Phenoxymethyl)piperazine

A 6 g portion of 1,4-bis(phenylmethyl)-2-piperazinemethanol was dissolved in 90 ml of dichloromethane together with 4.26 ml of triethylamine and then cooled to 0°–5° C. A 2.04 ml portion of methanesulfonyl chloride was added and the mixture was allowed to warm to room temperature over 2 hours. The mixture was washed with ice cold sodium bicarbonate solution, followed twice with ice water, dried, filtered and evaporated. The residue was dissolved in dimethylformamide and added to a solution of 2.07 g of sodium phenol and 1.02 g of 50% sodium hydride in 30 ml of dimethylformamide under argon. This mixture was stirred for 48 hours, water was added and the mixture extracted twice with ether. The extracts were combined, washed with water, dried, filtered and evaporated, giving a gum which was crystallized from methanol with refrigeration, giving 4.1 g of 3-phenoxymethyl-1,4-bis(phenylmethyl)piperazine.

The 4.1 g of the above compound was suspended in 150 ml of ethanol under argon. A 1 g portion of 10% palladium on carbon was added and the mixture hydrogenated at 40°–45° C. The mixture was then filtered and the solvents removed, giving 2 g of 3-phenoxymethyl-piperazine.

EXAMPLE 9

1-Ethyl-6-fluoro-1,4-dihydro-4-oxo-7-[3-(phenoxymethyl)-1-piperazinyl]-3-quinolinecarboxylic acid A mixture of 2 g of 3-phenoxymethylpiperazine and 701 mg of 7-chloro-1-ethyl-6-fluoro-1,4-dihydro-4-oxo-3-quinolinecarboxylic acid in 10 ml of pyridine was heated under argon in a pressure bottle at 130° C. for 18 hours. The solvents were removed and the residue chromatographed on silica gel, eluting with chloroform:methanol (9:1). The appropriate fractions were combined, evaporated, triturated with methanol and ether, then dried, giving 519 mg of the desired compound, mp 198°–200° C.

EXAMPLE 10

1-Ethyl-6-fluoro-1,4-dihydro-7-[3-(methoxymethyl)-4-methyl-1-piperazinyl]-4-oxo-3-quinolinecarboxylic acid A 200 mg portion of 1-ethyl-6-fluoro-1,4-dihydro-7-[3-(methoxymethyl)-1-piperazinyl]-4-oxo-3-quinolinecarboxylic acid was dissolved in a mixture of 0.6 ml of 37% formaldehyde and 0.75 ml of 90% formic acid, heated on a steam bath for 3 hours and then concentrated in vacuo. The residue was dissolved in 5 ml of water and 1N sodium hydroxide was added to pH 7. The resulting solid was collected, washed with water and dried, giving 180 mg of the desired product, mp 228°–230° C.

EXAMPLE 11

1-Ethyl-6-fluoro-1,4-dihydro-7-[4-methyl-3-(phenoxymethyl)-1-piperazinyl]-4-oxo-3-quinolinecarboxylic acid A 200 mg portion of 1-ethyl-6-fluoro-1,4-dihydro-4-oxo-7-[3-(phenoxymethyl)-1-piperazinyl]-3-quinolinecarboxylic acid was dissolved in a mixture of 0.6 ml of 37% formaldehyde and 0.75 ml of 90% formic acid, heated on a steam bath for 3 hours and then concentrated in vacuo. The residue was dissolved in 5 ml of water and 1N sodium hydroxide was added to pH 7. The resulting solid was collected, washed with water and dried, giving 188 mg of the desired product, mp 202°–204° C.

EXAMPLE 12

2-(5-Bromo-2-thienyl)piperazine

A 29.3 g portion of selenium dioxide was added to a mixture of 80 ml of dioxane and 10 ml of water and warmed to 55°–60° C. with stirring. A 50 g portion of 5-bromo-2-acetylthiophene was added, the mixture was refluxed 3.5 hours, cooled, diluted with dioxane, filtered and evaporated to dryness in vacuo. The residue was dissolved in dichloromethane, filtered and hexane was added to the filtrate. The solid was collected and the filtrate concentrated giving more solid making a total of 27.6 g of 5-bromo-2-thiopheneglyoxaldehyde.

A mixture of 23.7 g of the above thiophene derivative in 500 ml of ethanol was stirred and cooled to 0°–5° C. under argon. A solution of 6.6 g of ethylenediamine in 50 ml of ethanol was added dropwise. The temperature was maintained at 0°–5° C. until solution was complete, then the mixture was stirred at room temperature for 3.5 hours, recooled to 0°–5° C. and 7.6 g of sodium borohydride added. This mixture was stirred for 18 hours, water was added and the mixture evaporated to dryness in vacuo. The residue was dissolved in dichloromethane, washed with water, dried, filtered and evaporated giving an oil which solidified. The solid was dissolved in cold ether, filtered and concentrated in vacuo at 40° C. The solid was collected, washed with cold ether and dried, giving 8.9 g of 2-(5-bromo-2-thienyl)piperazine.

EXAMPLE 13

7-[3-(5-Bromo-2-thienyl)-1-piperazinyl]-1-ethyl-6-fluoro-1,4-dihydro-4-oxo-3-quinolinecarboxylic acid A 3 g portion of 2-(5-bromo-2-thienyl)piperazine was suspended in 8 ml of dry pyridine. An 820 mg portion of 7-chloro-1-ethyl-6-fluoro-1,4-dihydro-4-oxo-3-quinolinecarboxylic acid was added and the mixture was heated in a pressure bottle, under argon, at 120°–130° C. for 18 hours, then cooled, filtered and evaporated to dryness. The residue was evaporated from toluene and this residue purified by chromatography, eluting with chloroform:water saturated methanol (9:1). The appropriate fractions were combined, evaporated and recrystallized from dimethylformamide-ether, giving 440 mg of the desired product, mp 233°–235° C. (dec.).

EXAMPLE 14

7-[3-(5-Bromo-2-thienyl)-4-methyl-1-piperazinyl]-1-ethyl-6-fluoro-1,4-dihydro-4-oxo-3-quinolinecarboxylic acid A 150 mg portion of 7-[3-(5-bromo-2-thienyl)-1piperazinyl]-1-ethyl-6-fluoro-1,4-dihydro-4-oxo-3-quinolinecarboxylic acid was dissolved in a mixture of 0.6 ml of 37% formaldehyde and 0.75 ml of glacial acetic acid, heated on a steam bath for 2 hours and then evaporated. The residue was diluted with 3 ml of water, adjusted to pH 7 with 1N sodium hydroxide and the solid collected, giving 120 mg of the desired product, mp 243°–245° C. (dec.).

EXAMPLE 15

2-(3-Methyl-2-thienyl)piperazine

A 34.9 g portion of selenium dioxide was dissolved in a mixture of 85 ml of dioxane and 10 ml of water with stirring and heating to 55°–60° C. A 40 g portion of -acetyl-3-methylthiophene was added and the mixture was refluxed for 6 hours, then cooled, diluted with dioxane, filtered and evaporated to dryness. The residue was dissolved in ether and the crystals which formed collected, giving 12.03 g of 3-methyl-α-oxo-2-thiopheneacetaldehyde.

A 5 g portion of the above aldehyde was dissolved in 100 ml of ethanol, cooled to 0°–5° C. and a solution of 2.14 g of ethylenediamine in 10 ml of ethanol was added dropwise with stirring. The mixture was allowed to come to room temperature over 3 hours, then 2.4 g of sodium borohydride was added and the mixture was stirred for 18 hours. Water was added, then the mixture was concentrated. The residue was dissolved in dichloromethane, cooled, extracted with water, dried, filtered and evaporated to an oil which crystallized, giving 4.6 g of 2-(3-methyl-2-thienyl)piperazine.

EXAMPLE 16

1-Ethyl-6-fluoro-1,4-dihydro-7-[3-(3-methyl-2-thienyl)-1-piperazinyl]-4-oxo-3-quinolinecarboxylic acid A 3.64 g portion of 2-(3-methyl-2-thienyl)piperazine was added to 10 ml of pyridine followed by 1.35 g of 7-chloro-1-ethyl-6-fluoro-1,4-dihydro-4-oxo-3- quinolinecarboxylic acid. The mixture was placed in a pressure bottle, under argon, sealed and heated at 120°–130° C., with stirring for 18 hours. The solvent was removed and the residue purified by chromatography, eluting with chloroform:methanol (9:1), giving 135 mg of the desired product, mp 252°–255° C. (dec.).

EXAMPLE 17

2-(5-Chloro-2-benzofuranyl)piperazine

A 31.3 g portion of selenium dioxide was added to a mixture of 85 ml of dioxane and 11 ml of water. The mixture was stirred and heated to 55°–60° C., then 50 g of 2-acetyl-5-chlorobenzofuran was added and this mixture was heated at reflux for 4 hours. The mixture was diluted with warm dioxane, filtered and evaporated to dryness. The residue was refluxed with ether, then cooled, giving 45 g of 5-chloro-o-oxo-2-benzofuranacetaldehyde.

A 32 g portion of the above aldehyde was suspended in a mixture of 600 ml of ethanol and 60 ml of dioxane, cooled to 0°–5° C. and a solution of 10.1 g of ethylenediamine in 60 ml of ethanol was added dropwise. The mixture was allowed to come to room temperature over one hour, then stirred for 18 hours, cooled to 0°–5° C. and 11.7 g of sodium borohydride was added. This mixture was evaporated to dryness, ether was added and the solid collected, giving 3.05 g of 2-(5-chloro-2-benzofuranyl)piperazine.

EXAMPLE 18

7-[3-(5-Chloro-2-benzofuranyl)-1-piperazinyl]-1-ethyl-6-fluoro-1,4-dihydro-4-oxo-3-quinolinecarboxylic acid A 1.45 g portion of 2-(5-chloro-2-benzofuranyl)piperazine was added to 5 ml of pyridine. A 540 mg portion of 7-chloro-1-ethyl-6-fluoro-1,4-dihydro-4-oxo-3-quinolinecarboxylic acid was added and the mixture was heated in a sealed bottle, under argon, at 130°–135° C. for 18 hours, then cooled in an ice bath. The solid was collected, triturated with cold pyridine, dichloromethane, ether and dimethylformamide, giving 180 mg of the desired product, mp 262°–263° C.

EXAMPLE 19

2-(5-Chloro-3-methylbenzo[b]thien-2-yl)piperazine

A 27.2 g portion of selenium dioxide was dissolved in a mixture of 70 ml of dioxane and 9 ml of water at 55°–60° C. A 50 g portion of 2-acetyl-5-chloro-3-methylbenzothiophene was added and the mixture was refluxed for 22 hours. The mixture was diluted with 500 ml of dioxane and filtered while warm. Cooling gave 35.4 g of 5-chloro-3-methyl-α-oxobenzo[b]thiophene-2-carboxaldehyde.

A 30 g portion of the above aldehyde was suspended in a mixture of 600 ml of ethanol and 60 ml of dioxane and cooled to 0°–5° C. A solution of 8.31 g of ethylenediamine in 50 ml of ethanol was added dropwise, the mixture was stirred at 0°–5° C. for 10 minutes, 50 ml of dioxane was added and then the mixture was stirred at room temperature for 18 hours. The mixture was cooled to 5° C., 8.5 g of sodium borohydride added, the mixture was stirred and allowed to come to room temperature, then evaporated to dryness. The residue was dissolved in dichloromethane, water washed, dried, filtered and evaporated. The residue was added to ether and allowed to stand overnight. The resulting solid was purified by column chromatography, eluting with chloroform:methanol (9:1), giving 3.5 g of 2-(5-chloro-3-methylbenzo[b]thien-2-yl)piperazine.

EXAMPLE 20

7-[3-(5-Chloro-3-methylbenzo[b]thien-2-yl)-1-piperazinyl]-1-ethyl-6-fluoro-1,4-dihydro-4-oxo-3-quinolinecarboxylic acid A 3.0 g portion of 2-(5-chloro-3-methylbenzo[b]thien-2-yl)piperazine was added to 5 ml of pyridine. A 1.01 g portion of 7-chloro-1-ethyl-6-fluoro-1,4-dihydro-4-oxo-3-quinolinecarboxylic acid was added and the mixture was heated in a pressure bottle, under argon at 130°–135° C. for 18 hours, then cooled and placed in an ice bath. The resulting crystals were collected, washed with cold pyridine, dichloromethane and ether and recrystallized from dimethylformamide, giving 401 mg of the desired product, mp 300°–305° C.

EXAMPLE 21

2-(3-Methylbenzo[b]thien-2-yl)piperazine

A 52.9 g portion of 2-acetyl-3-methylbenzothiophene was added to a solution of 36.9 g of selenium dioxide in 95 ml of dioxane and 13 ml of water at 55°–60° C. The mixture was refluxed overnight, filtered, washed with dioxane and evaporated. The residue was purified by flash column chromatography, eluting with hexane:ethyl acetate (8:2), giving 5.1 g of 3-methyl-o-oxobenzo[b]thiophene-2-acetaldehyde.

A 5 g portion of the above aldehyde was dissolved in a mixture of 100 ml of ethanol and 10 ml of dioxane. To this mixture, in an ice bath was added a solution of 1.61 g of ethylenediamine in ethanol. The mixture was stirred for one hour at room temperature, recooled to 0°–5° C. and 2.04 g of sodium borohydride added. The mixture was stored at room temperature overnight, water was added and all the solvents were removed. The residue was extracted with dichloromethane, water washed, dried, filtered and evaporated. This residue was purified by flash column chromatography, eluting with chloroform:methanol (9:1), giving 2.39 g of 2-(3-methylbenzo[b]thien-2-yl)piperazine.

EXAMPLE 22

1-Ethyl-6-fluoro-1,4-dihydro-7-[3-(3-methylbenzo[b]-thien-2-yl)-1-oiperazinvl]-4-oxo-3-quinolinecarboxylic acid A 2 g portion of 2-(3-methylbenzo[b]thien-2-yl)piperazine was added to 7 ml of pyridine. A 780 mg portion of 7-chloro-1-ethyl-6-fluoro-1,4-dihydro-4-oxo-3-quinolinecarboxylic acid was added and the mixture was heated in a pressure bottle, under argon at 120°–130° C. for 18 hours. The solid was collected, washed with pyridine, then ether and recrystallized from dimethylformamide, giving 540 mg of the desired product, mp 302°–304° C. (dec.).

EXAMPLE 23

2-(Fluoromethyl)piperazine

A 50 g portion of 6,7-difluoroaniline and 83.7 g of diethyl ethoxymethylenemalonate were heated with stirring in an oil bath at 120° C. for 50 minutes. To this mixture was added 500 ml of diphenyl ether and this solution was heated at 250° C. for 50 minutes. The precipitated solid was collected and recrystallized from dimethylformamide, giving 25 g of 6,7-difluoro-4-hydroxy-3-quinolinecarboxylic acid ethyl ester.

A 20 g portion of the above ester was suspended in 400 ml of dimethylformamide, 27.3 g of potassium carbonate was added and this mixture was stirred at 90° C. A 61.8 g portion of ethyl iodide was added and this mixture was stirred at 90° C. for 24 hours and then evaporated. The residue was dissolved in water and then extracted with dichloromethane. The extract was washed with water, dried, filtered and evaporated in vacuo. The residue was recrystallized from ethanol, giving 16.15 g of 1-ethyl-6,7-difluoro-1,4-dihydro-4-oxo-3-quinolinecarboxylic acid, ethyl ester.

A 4.1 g portion of the above ester in 50 ml of 37% hydrochloric acid was refluxed overnight, then cooled, basified with sodium hydroxide and then acidified with glacial acetic acid. The solid was collected, washed with water, methanol, ether and dried, giving 3.6 g of 1-ethyl-6,7-difluoro-1,4-dihydro-4-oxo-3-quinolinecarboxylic acid.

1,4-Dibenzyl-2-piperazinecarboxylic acid ethyl ester was prepared by the method of E. Jucker and E. Rissi, Helv. Chem. Acta, 45, 2383 (1962) and converted to 1,4-bis(phenylmethyl)-2-piperazinemethanol according to the same reference procedure.

A 25 g portion of the above piperazinemethanol was dissolved in 50 ml of dichloromethane. This was slowly added to a solution of 25 g of diethylaminosulfurtrifluoride in 50 ml of dichloromethane stirring at −65° C. under an argon atmosphere. The reaction was slowly allowed to warm to room temperature and then continued to stir for 12 hours.

On workup, the reaction temperature was lowered to 5° C. while cold water was slowly added. Then 5N sodium hydroxide solution was slowly added until the aqueous portion achieved a pH of 9. The product was then thoroughly extracted with dichloromethane. The collected extracts were combined, dried and the solvent removed to yield an oil weighing 16.5 g as a mixture of two products. The desired product (most polar of the two) was isolated by silica gel flash column chromatography (13% diethylether-87% hexane eluent) and weighed 11 g.

The product of the above procedure, 1,4-dibenzyl-2-fluoromethylpiperazine, was dissolved in 30 ml of ethanol. To this was added 3.5 g of 10% palladium on carbon and the mixture was hydrogenated employing a Parr Shaker apparatus at 40° C. under 45 psi hydrogen pressure for 4 hours. The palladium on carbon mixture was filtered through diatomaceous earth and the ethanol was removed in vacuo to leave a colorless product consisting of 2.8 g of 2-(fluoromethyl)piperazine.

EXAMPLE 24

1-Ethyl-6-fluoro-7-[3-(fluoromethyl)-1-piperazinyl]-1,4-dihydro-4-oxo-3-quinolinecarboxylic acid A mixture of 400 mg of 2-(fluoromethyl)piperazine and 200 mg of 1-ethyl-6,7-difluoro-1,4-dihydro-4-oxo-3-quinolinecarboxylic acid in 3 ml of pyridine was stirred and heated at 75° C., under nitrogen, in a pressure bottle for 3 hours. The pyridine was removed and replaced with methanol. This mixture was chromatographed on silica gel, eluting with methanol:chloroform (2:8). The solid was recrystallized from methanol, giving 100 mg of the desired product, mp 177°-180° C.

EXAMPLE 25

1-Ethyl-6-fluoro-7-[3-(fluoromethyl)-4-methyl-1-piperazinyl]-1,4-dihydro-4-oxo-3-quinolinecarboxylic acid A 100 mg portion of 1-ethyl-6-fluoro-7-[3-(fluoromethyl)-1-piperazinyl]-1,4-dihydro-4-oxo-3-quinolinecarboxylic acid and 300 mg of sodium formate were dissolved in a mixture of 3 ml of glacial acetic acid and 3 ml of 37% formaldehyde and refluxed overnight. The mixture was cooled, basified with sodium hydroxide, acidified with glacial acetic acid and evaporated. The residue was triturated with hot chloroform and the solid crystallized from methanol, giving 91 mg of the desired product, mp 230°-235° C. (dec.).

EXAMPLE 26

1-Ethyl-6-fluoro-1,4-dihydro-4-oxo-7-[3-(2-thienyl)-1-piperazinyl]-3-quinolinecarboxylic acid Al mixture of 27.5 g of selenium dioxide, 160 ml of dioxane and 5.5 ml of water was heated at 55° C. until solution was complete. A 31.54 g portion of 2-acetylthiophene was added and the mixture was refluxed for 4 hours, then cooled, filtered and evaporated under reduced pressure. The residue was distilled giving 24.5 g of 2-thiopheneglyoxylaldehyde.

A solution of 8.2 g of ethylenediamine in 250 ml of ethanol was added to a solution of 17.64 g of the above aldehyde in 250 ml of ethanol at 0° C. This mixture was stirred at room temperature for 1.5 hours, recooled to 0° C. and 9.6 g of sodium borohydride was added. This mixture was stirred overnight, quenched with water and the ethanol removed. The residue was extracted with dichloromethane, washed with water, dried and evaporated. The residue was crystallized with ether-hexane, giving 12 g of 2-(2-thienyl)piperazine.

A mixture of 504 mg of the above piperazine, 269 mg of 7-chloro-1-ethyl-6-fluoro-1,4-dihydro-4-oxo-3-quinolinecarboxylic acid and 10 ml of pyridine was refluxed under argon for 24 hours, then cooled and evaporated under reduced pressure. The residue was triturated with ether, the solid collected, dissolved in 40% acetic acid and neutralized with 1N sodium hydroxide. The solid was collected, washed with methanol, ether and dried, giving 110 mg of the desired product, mp 232°-234° C.

EXAMPLE 27

2-(2-Furanyl)piperazine

A mixture of 55 g of selenium dioxide, 11 ml of water and 150 ml of dioxane was heated at 55° C. until solution was complete. A 55 g portion of 2-acetylfuran was added, the mixture was refluxed for 4 hours, then filtered and evaporated. The residue was dissolved in dichloromethane, treated with activated charcoal, filtered and evaporated. The residue was distilled, giving 28 g of α-oxo-2-furanacetaldehyde.

A solution of 10.25 g of ethylene diamine in 250 ml of ethanol was added to a solution of 19.53 g of the above aldehyde in 250 ml of ethanol at 0° C. The mixture was stirred at room temperature for 1.5 hours, then recooled to 0° C. and 9.6 g of sodium borohydride added. This mixture was stirred overnight, quenched with water and the ethanol removed. The residue was extracted with dichloromethane, washed with water, dried and the solvent evaporated. The residue was crystallized from hexaneether, giving 13.8 g of 2-(2-furanyl)piperazine.

EXAMPLE 28

1-Ethyl-6-fluoro-7-[3-(2-furanyl)-1-piperazinyl]-1,4-dihydro-4-oxo-3-quinolinecarboxylic acid A mixture of 2.508 g of 2-(2-furanyl)piperazine, 942 mg of 7-chloro-1-ethyl-6-fluoro-1,4-dihydro-4-oxo-3-quinolinecarboxylic acid and 10 ml of pyridine was refluxed for 24 hours, then the solvent was removed. The residue was triturated with ether and chloroform, the solid collected, dissolved in 40% acetic acid and adjusted to pH 7 with 1N sodium hydroxide. The resulting solid was collected, washed with methanol and ether and dried, giving 600 mg of the desired product, mp 198° C.

EXAMPLE 29

2- 3-Thienyl)piperazine

3-Acetylthiophene was reacted with selenium dioxide as described in Example 16 giving 2-thiopheneglyoxylaldehyde. This aldehyde was then reacted with ethylenediamine, also as described in Example 16 giving 2-(3-thienyl)piperazine.

EXAMPLE 30

1-Ethyl-6-fluoro-1,4-dihydro-4-oxo-7-[3-(3-thienyl)-1piperazinyl]-3-quinolinecarboxylic acid A mixture of 1 g of 2-(3-thienyl)piperazine and 538 mg of 7-chloro-1-ethyl-6-fluoro-1,4-dihydro-4-oxo-3-quinolinecarboxylic acid in 8 ml of pyridine was further reacted as described in Example 26 giving 220 mg of the desired product, mp 198°-200° C.

EXAMPLE 31

1-Ethyl-6-fluoro-1,4-dihydro-7-[4-methyl-3-(2-thienyl)-1-piperazinyl]-4-oxo-3-quinolinecarboxylic acid A mixture of 200 mg of 1-ethyl-6-fluoro-1,4-dihydro-4-oxo-7-[3-(2-thienyl)-1-piperazinyl]-3-quinolinecarboxylic acid, 0.3 ml of 37% formalin and 0.35 ml of 90% formic acid was refluxed for 2 hours, then evaporated. A 10 ml portion of water was added and the mixture neutralized with 1N sodium hydroxide. The solid was collected, washed with water, methanol, ether and dried, giving 170 mg of the desired product, mp 238°-240° C.

EXAMPLE 32

1-Ethyl-6-fluoro-7-[3-(2-furanyl)-4-methyl-1piperazinyl]-1,4-dihydro-4-oxo-3-quinolinecarboxylic acid The procedure of Example 31 was followed using 200 mg of 1-ethyl-6-fluoro-7-[3-(2-furanyl)-1-piperazinyl]-1,4-dihydro-4-oxo-3-quinolinecarboxylic acid, giving 135 mg of the desired product, mp 209°-212° C.

EXAMPLE 33

2-(5-Chloro-2-thienyl)piperazine

2-Chloro-5-acetylthiophene was reacted as described in Example 16, first with selenium dioxide, giving 1-(5-chloro-2-thienyl)-2,2-dihydroxyethanone and then with ethylene diamine and sodium borohydride, giving 2-(5-chloro-2-thienyl)piperazine.

EXAMPLE 34

7-[3-(5-Chloro-2-thienyl)-1-piperazinyl]-1-ethyl-6-fluoro-1,4-dihydro-4-oxo-3-quinolinecarboxylic acid A mixture of 2.424 g of 2-(5-chloro-2-thienyl)piperazine and 1.076 g of 7-chloro-1-ethyl-6-fluoro-1,4-dihydro-4-oxo-3-quinolinecarboxylic acid in 12 ml of pyridine was refluxed under argon for 24 hours and then cooled. The solid was collected, washed with methanol and ether, then dried giving 320 mg of the desired product, mp 232°-234° C.

EXAMPLE 35

1-Ethyl-6-fluoro-1,4-dihydro-7-[4-methyl-3-(3-thienyl)-1-piperazinyl]-4-oxo-3-quinolinecrboxylic acid The procedure of Example 31 was followed using 70 mg of 1-ethyl-6-fluoro-1,4-dihydro-4-oxo-7-[3-(3-thienyl)-1-piperazinyl]-3-quinolinecarboxylic acid, giving 50 mg of the desired product, mp 226°-228° C.

EXAMPLE 36

2-(5-Methyl-2-thienyl)piperazine

2-Acetyl-5-methylthiophene was reacted as described in Example 16, first with selenium dioxide, giving 2,2-dihydroxy-1-(5-methyl-2-thienyl)ethanone and then with ethylene diamine and sodium borohydride, giving 2-(5-methyl-2-thienyl)piperazine.

EXAMPLE 37

1-Ethyl-6-fluoro-1,4-dihydro-7-[3-(5-methyl-2-thienyl)-1-piperazinyl]-4-oxo-3-quinolinecarboxylic acid A mixture of 4.368 g of 2-(5-methyl-2-thienyl)piperazine and 2.152 g of 7-chloro-1-ethyl-6-fluoro-1,4-dihydro-4-oxo-3-quinolinecarboxylic acid in 15 ml of pyridine was heated at reflux under argon for 18 hours, then allowed to cool and the solvent removed. The residue was triturated with methanol and ether, then filtered and dried, giving 580 mg of the desired product, mp 200°-210° C. (dec.).

EXAMPLE 38

1-Ethyl-6-fluoro-1,4-dihydro-7-[4-methyl-3-(5-methyl-2-thieny)-1-piperazinyl]-4-oxo-3-quinolinecarboxylic acid The procedure of Example 31 was followed using mg of 1-ethyl-6-fluoro-1,4-dihydro-7-[3-(5-methyl-2-thienyl)-1-piperazinyl]-4-oxo-3-quinolinecarboxylic acid, giving 210 mg of the desired product, mp 224° C.

EXAMPLE 39

2-(4-Methyl-2-thienyl)piperazine

2-Acetyl-4-methylthiophene was reacted as described in Example 26, first with selenium dioxide, giving 2,2-dihydroxy-1-(4-methyl-2-thienyl)ethanone and then with ethylene diamine and sodium borohydride, giving 2-(4-methyl-2-thienyl)piperazine.

EXAMPLE 40

1-Ethyl-6-fluoro-1,4-dihydro-7-[3-(4-methyl-2-thienyl)-1-piperazinyl]-4-oxo-3-quinolinecarboxylic acid A mixture of 10.92 g of 2-(4-methyl-2-thienyl)piperazine and 5.38 g of 7-chloro-1-ethyl-6-fluoro-1,4-dihydro-4-oxo-3-quinolinecarboxylic acid in 30 ml of pyridine was heated at reflux under argon for 18 hours, then allowed to cool and the solvent removed. The residue

EXAMPLE 41

2-(5-Methyl-2-furanyl)piperazine

2-Acetyl-5-melthylfuran was reacted as described in Example 26, first with selenium dioxide, giving 2,2-dihydroxy-1-(5-methyl-2-furanyl)ethanone and then with ethylene diamine and sodium borohydride, giving 2-(5-methyl-2-furanyl)piperazine.

EXAMPLE 42

1-Ethyl-6-fluoro-1,4-dihydro-7-[3-(5-methyl-2-furanyl)-1-piperazinyl]-4-oxo-3-quinolinecarboxylic acid A mixture of 4.98 g of 2-(5-methyl-2-furanyl)piperazine and 2.69 g of 7-chloro-1-ethyl-6-fluoro-1,4-dihydro-4-oxo-3-quinolinecarboxylic acid in 10 ml of pyridine was refluxed for 48 hours and then evaporated. The residue was chromatographed on silica gel eluting with chloroform:methanol:water (9.5:0.5:0.02), giving 1.1 g of the desired product, mp 186°–188° C.

EXAMPLE 43

1-(Phenylsulfonyl)-3-(2-piperazinyl)-1H-pyrrole

To a suspension of 1.056 g of prewashed sodium hydride in 50 ml of dimethylformamide at 0° C. was added dropwise a solution of 1.34 g of pyrrole in 50 ml of dimethylformamide. The mixture was stirred for 30 minutes, then a solution of 3.89 g of benzenesulfonyl chloride in dimethylformamide was added. This mixture was stirred at room temperature for 18 hours, then slowly quenched with water and extracted several times with ether. The extracts were combined, washed with water, dried and evaporated, giving 2.9 g of 1-(phenylsulfonyl)-1H-pyrrole.

A mixture of 41.4 g of 1-(phenylsulfonyl)-1H-pyrrole, prepared as described above, and 17.16 g of acetyl chloride in 200 ml of dichloroethane was added to a suspension of 32 g of aluminum chloride in 200 ml of dichloroethane. The reaction was stirred for one hour, poured onto a mixture of ice and concentrated hydrochloric acid and extracted several times with ether. The extracts were combined and evaporated. The residue was triturated with ether and the solid collected, giving 39 g of 3-acetyl-1-(phenylsulfonyl)-1H-pyrrole.

A 49.8 g portion of 3-acetyl-1-(phenylsulfonyl)-1H-pyrrole, prepared as described above, was reacted as described in Example 26, first with selenium dioxide, giving 3-(dihydroxyacetyl)-1-(phenylsulfonyl)-1H-pyrrole and then with ethylene diamine and sodium borohydride, giving 1-(phenylsulfonyl)-3-(2-piperazinyl)-1H-pyrrole.

EXAMPLE 44

1-Ethyl-6-fluoro-1,4-dihydro-4-oxo-7-[3-[1-(phenylsulfonyl)-1H-pyrrol-3-yl]-1-piperazinyl]-3-quinolinecarboxylic acid A mixture of 4.365 g of 1-(phenylfulsonyl)-3-(2-piperazinyl)-1H-pyrrole, 1.345 g of 7-chloro-1-ethyl-6-fluoro-1,4-dihydro-4-oxo-3-quinolinecarboxylic acid and ml of pyridine was heated in a pressure bottle for 24 hours, then cooled and the solvent removed under reduced pressure. The residue was purified by chromatography on silica gel, eluting with chloroform:methanol:water:triethylamine (95:5:1:1), giving 950 mg of the desired product, mp 120° C.

EXAMPLE 45

2-(2-Benzofuranyl)piperazine

Benzofuran-2-yl methyl ketone was reacted as described in Example 26, first with selenium dioxide, giving 2,2-dihydroxy-1-(2-benzoufranyl)ethanone and then with ethylene diamine and sodium borohydride, giving 2-(2-benzofuranyl)piperazine.

EXAMPLE 46

7-[3-(2-Benzofuranyl)-1-piperazinyl]-1-ethyl-6-fluoro-1,4-dihydro-4-oxo-3-quinolinecarboxylic acid A mixture of 6.06 g of the above piperazine, 2.69 g of 7-chloro-1-ethyl-6-fluoro-1,4-dihydro-4-oxo-3-quinolinecarboxylic acid and 18 ml of pyridine was heated at reflux for 48 hours, then cooled and the solvent removed under reduced pressure. The residue was crystallized from chloroform:methanol (9:1), giving 710 mg of the desired product, mp 226°–228° C.

EXAMPLE 47

2-(2,5-Dimethyl-3-thienyl)piperazine

3-Acetyl-2,5-dimethylthiophene was reacted as described in Example 26, first with selenium dioxide, giving 1-(2,5-dimethyl-3-thienyl)-2,2-dihydroxyethanone and then with ethylene diamine and sodium borohydride, giving 2-(2,5-dimethyl-3-thienyl)piperazine.

EXAMPLE 48

7-[3-(2,5-Dimethyl-3-thienyl)-1-piperazinyl]-1-ethyl-6-fluoro-1,4-dihydro-4-oxo-3-quinolinecarboxylic acid A mixture of 2.35 g of 2-(2,5-dimethyl-3-thienyl)piperazine and 1.076 g of 7-chloro-1-ethyl-6-fluoro-1,4-dihydro-4-oxo-3-quinolinecarboxylic acid in 10 ml of pyridine was heated for 48 hours, then cooled and filtered. The filtrate was evaporated under reduced pressure and the residue triturated with chloroform:methanol (9:1),. giving mg of the desired product, mp 248°–250° C.

EXAMPLE 49

1-Ethyl-6-fluoro-1,4-dihydro-7-[4-methyl-3-[1-phenylsulfonyl)-1H-pyrrol-3-yl]-1-piperazinyl]-4-oxo-3-quinolinecarboxylic acid 1-Ethyl-6-fluoro-1,4-dihydro-4-oxo-7-[3-[1-(phenylsulfonyl)-1H-pyrrol-3-yl]-1-piperazinyl]-3-quinolinecarboxylic acid was reacted as described in Example 31, giving 1 g of the desired product, mp 120° C.

EXAMPLE 50

2-(2,5-Dichloro-3-thienyl)piperazine

A 31.4 g portion of selenium dioxide was added to a solution of 75 ml of dioxane and 10 ml of water and warmed to 60° C. with stirring. A 50 g portion of 2-acetyl-2,5-dichlorothiophene was added and the mixture was stirred at reflux for 7 hours. The mixture was diluted with dioxane, filtered and evaporated to dryness. Ether was added, then heptane and the mixture refrigerated. The solid was collected, giving 30.1 g of 2,5-dichloro-α-oxo-3-thiopheneacetaldehyde.

A 10.45 g portion of the above aldehyde was suspended in 200 ml of ethanol, cooled to 0°–5° C. and a solution of 3.3 g of ethylenediamine in 20 ml of ethanol added dropwise with stirring. The mixture was allowed to come to room temperature over 3 hours, then 3.8 g of sodium borohydride was added and the mixture was evaporated to dryness. The residue was dissolved in dichloromethane, water washed, filtered, dried and evaporated. The resulting gum was triturated with ether producing an oil. The oil was purified by chromatography, eluting with chloroform:methanol (9:1), giving an oil which crystallized, giving 3.3 g of 2-(2,5-dichloro-3-thienyl)piperazine.

EXAMPLE 51

7-[3-(2,5-Dichloro-3-thienyl)-1-piperazinyl]-1-ethyl-6-fluoro-1,4-dihydro-4-oxo-3-quinolinecarboxylic acid A 3.1 g portion of 2-(2,5-dichloro-3-thienyl)piperazine was dissolved in 8 ml of pyridine, 880 mg of 7-chloro-1-ethyl-6-fluoro-1,4-dihydro-4-oxo-3-quinolinecarboxylic acid was added and the mixture was heated, under argon, in a pressure bottle, at 120°–130° C. for 18 hours. After cooling, the solid was collected, washed with ethanol, dried and recrystallized from dimethylformamide, giving 171 mg of the desired product, mp 254°–256° C. (dec.).

EXAMPLE 52

N-Methyl-2-piperazinemethanamine

To a solutioen of 180 ml of dioxane and 72 ml of water was added 9 g of 2-chloromethyl-1,4-bis(phenylmethyl)piperazine, 4.3 g of potassium carbonate and 13.8 g of N-methyl, N-benzylamine. This mixture was stirred and heated at 80°–90° C. for 18 hours, then evaporated to a gum. Water and dichloromethane were added, the organic layer was separated, dried, filtered and evaporated giving 16.5 g of yellow oil. This oil was dissolved in 200 ml of ethanol, 20 ml of water and 4 g of 10% palladium on carbon were added and the mixture was hydrogenated for 36 hours, then filtered. The filtrate was evaporated, giving 4.4 g of N-methyl-2-piperazinemethanamine.

EXAMPLE 53

1-Ethyl-6-fluoro-1,4-dihydro-7-[3-[(methylamino)methyl]-1-piperazinyl]-4-oxo-3-quinolinecarboxylic acid, dihydrochloride A mixture of 1.0 g of N-methyl-2-piperazinemethanamine, 653 mg of 1-ethyl-6,7-difluoro-1,4-dihydro-4-oxo-3-quinolinecarboxylic acid and 5 ml of pyridine was heated in a pressure bottle filled with argon for 18 hours at 75°–80° C. in an oil bath, then cooled and the excess solvent removed. The residue was evaporated twice from toluene and then purified by chromatography, giving 65 mg of white crystals. A 20 mg portion of these crystals was dissolved in one drop of concentrated hydrochloric acid and ethanol was added. The white crystals which separated were collected, giving 21 mg of the desired product, mp 265°–267° C. (dec.).

EXAMPLE 54

1-Ethyl-6-fluoro-1,4-dihydro-7-[4-methyl-3-(3-methylbenzo[b]thien-2-yl)-1-piperazinyl]-4-oxo-3-quinolinecarboxylic acid A 150 mg portion of 1-ethyl-6-fluoro-1,4-dihydro-7-[3-(3-methylbenzo[b]thien-2-yl)-1-piperazinyl]-4-oxo-3-quinolinecarboxylic acid was suspended in 0.6 ml of 37% formaldehyde and 0.75 ml of 90% formic acid was added. The mixture was heated on a steam bath for 2 hours, then cooled, evaporated and 5 ml of water added. The mixture was adjusted to pH 7 with 1N sodium hydroxide and the solid collected, washed with water and dried, giving 143 mg of the desired product, mp 253°–254° C.

EXAMPLE 55

7-[3-(5-Chloro-2-benzofuranyl)-4-methyl-1-piperazinyl]-1-ethyl-6-fluoro-1,4-dihydro-4-oxo-3-quinolinecarboxylic acid A 150 mg portion of 7-[3-(5-chloro-2-benzofuranyl)-1-piperazinyl]-1-ethyl-6-fluoro-1,4-dihydro-4-oxo-3-quinolinecarboxylic acid was suspended in 0.6 ml of 37% formaldehyde and 0.75 ml of 90% formic acid was added. The mixture was heated on a steam bath for 2 hours, then evaporated to dryness. A 5 ml portion of water was added, the pH adjusted to 7.0 with 1N sodium hydroxide and the solid collected, washed with water and dried, giving 113 mg of the desired product, mp 248°–249° C.

EXAMPLE 56

1-Ethyl-6-fluoro-1,4-dihydro-4-oxo-7-[3-(1H-pyrrol-3-yl)-1-piperazinyl]-3-quinolinecarboxylic acid A mixture of 299 mg of 1-ethyl-6-fluoro-1,4-dihydro-4-oxo-7-[3-[1-(phenylsulfonyl)-1H-pyrrol-3-yl]-1-piperazinyl]-3-quinolinecarboxylic acid 3 ml of 1N sodium hydroxide and 10 ml of dioxane was heated at 100° C. for 4 hours, then allowed to cool and neutralized to pH 7 with 10% acetic acid. The solvents were evaporated until a solid formed. This solid was collected, washed with water, methanol and ether and dried, giving 180 mg of the desired product, mp 220° C.

EXAMPLE 57

1-(Phenylsulfonyl)-3-(2-piperazinyl)-1H-indole

To a solution of 41.39 g of 3-acetyl indole in 300 ml of dimethyl sulfoxide at 0° C. was added a solution of 18.6 g of potassium hydroxide in 20 ml of water. This mixture was stirred at 0° C. for 2 hours, then 47.6 ml of benzenesulfonyl chloride was added dropwise over 40 minutes. The mixture was stirred for an additional 30 minutes, then poured into aqueous ammonium chloride and extracted several times with ether. The ether extracts were combined, washed with water, dried and evaporated, giving 59.8 g of 3-acetyl-N-phenylsulfonyl indole.

A 24.42 g portion of selenium dioxide was added to a mixture of 32 ml of dioxane and 4 ml of water and warmed to 55°–60° C. with stirring. A 59.8 g portion of 3-acetyl-N-phenylsulfonyl indole was added, the mixture was refluxed 3.5 hours, cooled, diluted with dioxane, filtered and evaporated to dryness in vacuo. The residue was dissolved in dichloromethane, filtered and hexane was added to the filtrate. The solid was collected and the filtrate concentrated giving more solid, making a total of 19.1 g of 3-dihydroxyacetyl-N-phenylsulfonyl indole.

The 19.1 g of the above indole derivative in 500 ml of ethanol and 200 ml of dioxane was stirred and cooled to 0°–5° C. under argon. A solution of 3.46 g of ethylenediamine in 100 ml of ethanol was added dropwise. The temperature was maintained at 0°–5° C. until solution was complete, then the mixture was stirred at room temperature for 3.5 hours, recooled to 0°–5° C. and 4.37 g of sodium borohydride added. This mixture was stirred for 18 hours, water was added and the mixture evaporated to dryness in vacuo. The residue was dissolved in dichloromethane, washed with water, dried, filtered and evaporated giving an oil, which solidified. The solid was dissolved in cold ether, filtered and concentrated in vacuo at 40° C. The solid was collected, washed with cold ether and dried, giving 5 g of 1-(phenylsulfonyl)-3-(2-piperazinyl)-1H-indole.

EXAMPLE 58

1-Ethyl-6-fluoro-1,4-dihydro-7-[3-(1H-indol-3-yl)-1-piperazinyl]-4-oxo-3-quinolinecarboxylic acid A mixture of 4.092 g of 1-(phenylsulfonyl)-3-(2-piperazinyl)-1H-indole and 1.012 g of 1-ethyl-6,7-difluoro1,4-dihydro-4-oxo-3-quinolinecarboxylic acid in 5 ml of pyridine was heated at 95° C. for 3 hours, then cooled and the solid collected, washed with methanol and ether, giving 1.94 g of 1-ethyl-6-fluoro-1,4-dihydro-4-oxo-7-[3-[1-(phenylsulfonyl)-1H-indol-3-yl]-1-piperazinyl]-3-quinolinecarboxylic acid.

A mixture of 574 mg of 1-ethyl-6-fluoro-1,4-dihydro-4-oxo-7-[3-[1-(phenylsulfonyl)-1H-indol-3-yl]-1-piperazinyl]-3-quinolinecarboxylic acid, 10 ml of 1N sodium hydroxide and 20 ml of dioxane was reacted as described in Example 56, giving 280 mg of the desired product, mp 230° C.

EXAMPLE 59

1-Ethyl-6-fluoro-1,4-dihydro-7-[4-methyl-3-(1H-pyrrol-3-yl)-1-piperazinyl]-4-oxo-3-quinolinecarboxylic acid A mixture of 538 mg of 1-ethyl-6-fluoro-1,4-dihydro-7-[4-methyl-3-[1-(phenylsulfonyl)-1H-pyrrol-3-yl]-1-piperazinyl]-4-oxo-3-quinolinecarboxylic acid, 5 ml of 1N sodium hydroxide and 15 ml of dioxane was reacted as described in Example 56, giving 290 mg of the desired product, mp 150°-152° C.

EXAMPLE 60

1-Cyclopropyl-6-fluoro-1,4-dihydro-4-oxo-7-[3-(3-thienyl-1-piperazinyl]-3-quinolinecarboxylic acid A mixture of 229.6 g of 1,3-dichloro-4-fluorobenzene and 205.34 g of aluminum chloride was heated at 80° C. A 56 g portion of acetic anhydride was added dropwise over 2 hours, then the reaction was heated at 100° C. for 8 hours, poured onto a mixture of concentrated hydrochloric acid and ice and extracted several times with ether. The ether extracts were combined, washed with water, dried and the solvents evaporated. The solid was purified by vacuum distillation, giving 156.63 g of 6-acetyl-1,3-dichloro-4-fluorobenzene.

To a suspension of prewashed sodium hydride (76.8 g) in ether was added 189 g of diethylcarbonate. The mixture was heated to reflux and a solution of 131.84 g of 6-acetyl-1,3-dichloro-4-fluorobenzene in 1500 ml of ether was added dropwise over 5 hours. The mixture was then refluxed 24 hours, cooled, poured onto a mixture of ice and acetic acid and extracted several times with ether. The ether extracts were combined, washed with water, dried and evaporated. The residue was purified by vacuum distillation giving 80 g of ethyl 2,4-dichloro-5-fluorobenzoylacetate.

A mixture of 27.8 g of the above ester, 22.23 g of triethyl orthoformate and 25.52 g of acetic anhydride was heated at 150° C. for 2 hours and then evaporated under reduced pressure. A 30 g portion of the residue was dissolved in 100 ml of ethanol and 5.63 g of cyclopropylamine was added producing an exotherm. The mixture was stirred for one hour, then evaporated under reduced pressure, hexane added and the solid collected and dried. A solution of 17.25 g of this solid in a mixture of 2.64 g of 50% sodium hydride and 80 ml of dioxane was stirred at room temperature for 30 minutes, then heated at reflux for 2 hours and cooled. The mixture was neutralized with 1.5N potassium hydroxide and the product, 7-chloro-1-cyclopropyl-6-fluoro-1,4-dihydro-4-oxo-3-quinolinecarboxylic acid, collected.

A mixture of 562 mg of the above compound, 1.68 g of 3-thienylpiperazine and 8 ml of pyridine was heated at 130° C., in a pressure bottle, for 2 hours, The solvent was removed and the residue purified by chromatography on silica gel, eluting with chloroform:methanol:water:triethylamine (95:5:.1:.1), giving 275 mg of the desired product, mp 192°-194° C.

EXAMPLE 61

1-Ethyl-6,8-difluoro-1,4-dihydro-7-(4-methyl-1-piperazinyl)-4-oxo-3-quinolinecarboxylic acid A 49.1 g portion of 6,7,8-trifluoro-1,4-dihydro-4-oxo-3-quinolinecarboxylic acid, ethyl ester was reacted with 85 g of potassium carbonate, 266 g of ethyl iodide and 600 ml of dimethylformamide, giving 1-ethyl-1,4-dihydro-6,7,8-trifluoro-4-oxo-3-quinolinecarboxylic acid, ethyl ester.

A mixture of 17.7 g of the above ester was refluxed in 150 ml of 37% hydrochloric acid for 2 hours, giving 10 g of 1-ethyl-1,4-dihydro-6,7,8-trifluoro-4-oxo-3-quinolinecarboxylic acid, mp 240° C. (dec.).

A mixture of 500 mg of the above acid, 900 mg of N-methylpiperazine and 5 ml of pyridine was heated at 95° C., under argon for 30 minutes, giving 215 mg of the desired product, mp 240°-250° C. (dec.).

EXAMPLE 62

1-Cyclopropvl-6-fluoro-7-[3-(2-furanyl)-1-piperazinyl]-1,4-dihydro-4-oxo-3-quinolinecarboxylic acid A mixture of 843 mg of 7-chloro-1-cyclopropyl-6-fluoro-1,4-dihydro-4-oxo-3-quinolinecarboxylic acid, 2.28 g of 2-furanylpiperazine and 10 ml of pyridine was heated in a pressure bottle for 24 hours, then cooled first to room temperature and then at 0° C. The pyridine was removed under reduced pressure and the residue purified by flash column chromatography using chloroform:methanol:water:triethylamine (95:5:.1:.1), giving 280 mg of the desired product, mp 176° C.

EXAMPLE 63

(racemic)-N-Ethyl-6,8-difluoro-7-[3-(fluoromethyl)-1-piperazinyl]-1,4-dihydro-4-oxo-3-quinolinecarboxylic acid A mixture of 500 mg of 1-ethyl-1,4-dihydro-6,7,8-trifluoro-4-oxo-3-quinolinecarboxylic acid, 650 mg of racemic 3-fluoromethylpiperazine and 5 ml of pyridine was stirred at 80° C. in a sealed bottle under nitrogen for 2.5 hours. The solvents were removed and the residue triturated with methanol. The solid was collected, washed with methanol and dried, giving 376 mg of the desired product, mp 230°-235° C. (dec.).

EXAMPLE 64

(−)-N-Ethyl-6,8-difluoro-7-[3-(fluoromethyl)-1-piperazinyl]-1,4-dihydro-4-oxo-3-quinolinecarboxylic acid A 650 mg portion of 3-fluoromethylpiperazine (derived from the corresponding alcohol $[\alpha]_D = +55°$) was reacted as described in Example 63, giving 601 mg of the desired product, mp 240°-244° C. (dec.).

EXAMPLE 65

(+)-N-Ethyl-6,8-difluoro-7-[3-(fluoromethyl)-1-piperazinyl]-1,4-dihydro-4-oxo-3-quinolinecarboxylic acid A 650 mg portion of 3-fluoromethylpiperazine (derived from the corresponding alcohol $[\alpha]_D = -66° \pm 1°$) was reacted as described in Example 63, giving 572 mg of the desired product, mp 240°-245° C. (dec.).

EXAMPLE 66

1-Cyclopropyl-6-fluoro-1,4-dihydro-4-oxo-7-[4-methyl-3-(3-thienyl)-1-piperazinyl]-3-quinolinecarboxylic acid A mixture of 1.124 g of 7-chloro-1-cyclopropyl-6-fluoro-1,4-dihydro-4-oxo-3-quinolinecarboxylic acid, 2.688 g of 3-thienylpiperazine and 12 ml of pyridine was reacted as described in Example 60, giving 900 mg of 1-cyclopropyl-6-fluoro-1,4-dihydro-4-oxo-7-[3-(3-thienyl)-1-piperazinyl]-3-quinolinecarboxylic acid.

A 207 mg portion of the above compound was then reacted as described in Example 55, giving 150 mg of the desired product, mp 230° C.

EXAMPLE 67

6-Fluoro-1-(4-fluorophenyl)-7-[3-(2-furanyl)-1-piperazinyl]-1,4-dihydro-4-oxo-3-quinolinecarboxylic acid A mixture of 50.04 g of 6-acetylcarb-oxylic acid-1,3-dichloro-4-fluorobenzene, 40.014 g of triethyl orthoformate and 45.945 g of acetic anhydride was heated at 150° C. for 2 hours; then the excess reagents were removed. A mixture of 33.4 g of the above residue, 12.2 g of 4-fluoroaniline and 100 m: of ethanol was stirred for one hour, then hexane was added and the solid was collected, washed with hexane and dried, giving (Z)-2,4-dichloro-5-fluoro-α-[[(4-fluorophenyl)amino]methylene]-β-oxobenzenepropanoic acid, ethyl ester.

A mixture of 1 g of the above compound, 5 g of potassium carbonate and 40 ml of methyl ethyl ketone was refluxed for 16 hours, filtered while hot and washed with hot ethyl acetate. The filtrate was concentrated, the residue dissolved in chloroform, washed with water, dried and the solvent removed, giving 730 mg of 7-chloro-6-fluoro-1-(4-fluorophenyl)-1,4-dihydro-4-oxo-3-quinolinecarboxylic acid, ethyl ester.

A mixture of 320 mg of the above ester, 5 ml of 1N sodium hydroxide, 5 ml of water and 5 ml of ethanol was heated for 30 minutes, then cooled and adjusted to pH 7 with dilute hydrochloric acid. The solid was collected, giving 280 mg of 7-chloro-6-fluoro-1-(4-fluorophenyl)-1,4-dihydro-4-oxo-3-quinolinecarboxylic acid.

A mixture of 201 mg of the above compound, 365 mg of 2-furanylpiperazine and 5 ml of pyridine was heated at 130° C. in a pressure bottle for 16 hours, then cooled and the solvent removed. The residue was purified by chromatography as described in Example 62, giving 70 mg of the desired product, mp 242° C.

EXAMPLE 68

2-(1H-Pyrrol-1-ylmethyl)piperazine

A 10 g portion of 1,4-bis(phenylmethyl)-2-piperazinemethanol was dissolved in 150 ml of dichloromethane, 7.2 ml of t.irethylamine was added and the mixture was stirred and cooled in an ice bath to 0°-5° C. A 3.2 ml portion of methane sulfonyl chloride was added, the mixture was stirred and allowed to come to room temperature, then stirred overnight. The mixture was washed with cold sodium bicarbonate, twice with ether, then ice cold water, dried filtered and evaporated at 40° C. in vacuo to a gum.

A solution of 2.75 g of sodium pyrrole in 25 ml of dimethylformamide was added dropwise, under argon, with rapid stirring to a previously hexane washed solution of 2.96 g of sodium hydride in 100 ml of dimethylformamide in an ice bath. This solution was stirred for 2 hours, then a solution of the above gum in 25 ml of dimethylformamide was added dropwise. This mixture was stirred for 72 hours, then water was cautiously added and the mixture extracted with ether. The ether extract was washed twice with water, dried, filtered and evaporated to an oil. The oil was purified by chromatography, giving 2.5 g of solid which was dissolved in dichloromethane, filtered through hydrous magnesium silicate and evaporated, giving 2.4 g of 1,4-bis(-phenylmethyl)-2-(1H-pyrrol-1-ylmethyl)piperazine.

A 2.3 g portion of the above compound was dissolved in a mixture of 50 ml of ethanol and 5 ml of water, 0.6 g of 10% palladium on carbon was added and the mixture was hydrogenated at 45° C. for 4 hours, then filtered. The filtrate was evaporated, the residue dissolved in dichloromethane, filtered and reevaporated, giving 1.1 g of 2-(1H-pyrrol-1-ylmethyl)piperazine.

EXAMPLE 69

1-Ethyl-6-fluoro-1,4-dihydro-4-oxo-7-[3-(1H-pyrrol-1-ylmethyl)-1-piperazinyl]-3-quinolinecarboxylic acid A 1 g portion of 2-(1H-pyrrol-1-ylmethyl)piperazine and 0.76 g of 1-ethyl-6,7-difluoro-1,4-dihydro-4-oxo-3-quinolinecarboxylic acid were heated at 70°-75° C. in a sealed pressure bottle, filled with argon, for 18 hours, then ether was added and the solid collected, washed with ether and purified by chromatography, giving 595 mg of the desired product, mp 185°-188° C.

EXAMPLE 70

2-[(1-Methylethoxy)methyl]piperazine

A 12 g portion of 1,4-bis phenylmethyl)-2-piperazinemethanol, 696 mg of tetrabutyl ammonium hydrogen sulfate and 10.38 g of 2-iodopropane were added to 60 ml of 50% sodium hydroxide. The mixture was stirred and heated at 70°-80° C. for 3 hours, 6.11 ml of 2-iodopropane was added, stirring continued at 70°-80° C. overnight, 6.11 ml of 2iodopropane and 690 mg of tetrabutyl ammonium hydrogen sulfate were added and stirring continued at 70°-80° C. overnight. Dichloromethane was added, the organic layer separated, washed twice with water, dried, filtered and evaporated, giving an oil. This oil was purified by chromatography, giving 6.4 g of oil.

A 6.3 g portion of this oil and 1.6 g of 10% palladium on carbon were added to a mixture of 150 ml of ethanol and 10 ml of water, hydrogenated for 4 hours, then warmed to 40° C. and hydrogenated until there was no further uptake of hydrogen. The mixture was filtered, the filtrate evaporated to an oil which was reevaporated from ethanol. This residue was dissolved in dichloromethane, filtered and reevaporated, giving 3.1 g of 2-[(1-methylethoxy)methyl]piperazine.

EXAMPLE 71

1-Ethyl-6-fluoro-1,4-dihydro-7-[3-[(1-methylethoxy)-methyl]-1-piperazinyl]-4-oxo-3-quinolinecarboxylic acid A mixture of 2 g of 2-[(1-methylethoxy)methyl]-piperazine, 1.27 g of 1-ethyl-6,7-difluoro-1,4-dihydro-4-oxo-3-quinolinecarboxylic acid and 5 ml of pyridine was heated at 80° C. for 3 hours, then evaporated in vacuo. The residue was reevaporated three times from toluene, giving a gum. Ether was added to the gum which solidified. The solid was triturated with ether containing methanol and then dried giving 2.1 g of solid. A 1 g portion was purified by chromatography, giving 650 mg of the desired product, mp 144°–146° C.

EXAMPLE 72

1-Ethyl-6-fluoro-1,4-dihydro-7-[4-methyl-3-[(1-methylethoxy)methyl]-1-piperazinyl]-4-oxo-3-quinolinecarboxylic acid A 150 mg portion of 1-ethyl-6-fluoro-1,4-dihydro-7-[3-[(1-methylethoxy)methyl]-1-piperazinyl]-4-oxo-3-quinolinecarboxylic acid was dissolved in 0.6 ml of 37% formaldehyde and 0.75 ml of 90% formic acid, heated on a steam bath for one hour and then evaporated. A 5 ml portion of water was added, the solution neutralized with 5N sodium hydroxide and the solid collected, giving 76 mg of the desired product, mp 184°–186° C.

EXAMPLE 73

2-[(Dodecyloxy)methyl]piperazine

A 9.8 g portion of hexane washed 50% sodium hydride was suspended in 100 ml of dry dimethylformamide under argon. A 10 g portion of 1,4-bis(phenylmethyl)-2-piperazinemethanol was added, the mixture was stirred under argon for 30 minutes, then 24.97 g of dodecyl iodide was added dropwise. The mixture was heated at 80°–90° C. for 18 hours, then decomposed with water and extracted twice with ether. The extracts were combined, washed twice with water, dried, filtered and evaporated, giving an oil. This oil was purified by chromatography, giving 8.5 g of 2-[(dodecyloxy)methyl]-1,4-bis(phenylmethyl)piperazine.

An 8 g portion of the above piperazine in 130 ml of ethanol and 10 ml of water was hydrogenated with 10% palladium on carbon for 4 hours then filtered and the filtrate evaporated, giving 4.5 g of 2-[(dodecyloxy)methyl]piperazine.

EXAMPLE 74

7-[3-[(Dodecyloxy)methyl]-1-piperazinyl]-1-ethyl-6-fluoro-1,4-dihydro-4-oxo-3-quinolinecarboxylic acid A 710 mg portion of 1-ethyl-6,7-difluoro-1,4-dihydro-4-oxo-3-quinolinecarboxylic acid was suspended in 5 ml of pyridine and 2 g of 2-[(dodecyloxy)methyl]piperazine added. This mixture was heated at 80°–85° C. for 4 hours, then cooled and diluted with ether. The solid was collected, washed with ether and dried, giving 1.3 g of the desired product, mp 125°–127° C.

EXAMPLE 75

7-[3-[(Dodecyloxy)methyl]-4-methyl-1-piperazinyl]-1-ethyl-6-fluoro-1,4-dihydro-4-oxo-3-quinolinecarboxylic acid A 300 mg portion of 7-[3-[(dodecyloxy)methyl]-1-piperazinyl]-1-ethyl-6-fluoro-1,4-dihydro-4-oxo-3-quinolinecarboxylic acid was dissolved in a mixture of 1.2 ml of 37% formaldehyde and 1.5 ml of 90% formic acid, heated on a steam bath for 45 minutes and then evaporated in vacuo. A 5 ml portion of water was added, the solution neutralized with aqueous sodium hydroxide and the solid collected, washed with water and dried, giving 260 mg of the desired product, mp 166°–168° C.

EXAMPLE 76

2-[(Hexyloxy)methyl]piperazine

A 9.8 g portion of hexane washed 50% sodium hydride was added to 100 ml of dry dimethylformamide. A 10 g portion of 1,4-bis(phenylmethyl)-2-piperazinemethanol was added and the mixture was stirred for one hour, under argon. A 13.92 g portion of n-hexyl bromide was added, the mixture was stirred at 70° C. for 3 hours, decomposed with water dropwise under argon and extracted with ether. The ether extract was washed with water, dried, filtered and evaporated giving 14 g of a gum. The gum was dissolved in a mixture of 200 ml of ethanol and 10 ml of water and hydrogenated over 3.25 g of 10% palladium on carbon at 35°–40° C. for 4 hours, then filtered. The filtrate was evaporated, giving 7.1 g of 2-[(hexyloxy)methyl]piperazine as an oil.

EXAMPLE 77

1-Ethyl-6-fluoro-7-[3-[(hexyloxy)methyl]-1-piperazinyl]-1,4-dihydro-4-oxo-3-quinolinecarboxylic acid A 3 g portion of 2-[(hexyloxy)methyl]piperazine was added to 20 ml of pyridine in a pressure bottle, under argon. A 1.26 g portion of 1-ethyl-6,7-difluoro-1,4-dihydro-4-oxo-3-quinolinecarboxylic acid was added, the bottle sealed and the mixture heated at 80°–90° C. for 4 hours, then evaporated. The residue was evaporated twice from toluene, the residue triturated with ether and the solid collected, giving 2.03 g of the desired product, mp 12°–124° C.

EXAMPLE 78

1-Ethyl-6-fluoro-7-[3-[(hexyloxy)methyl]-4-methyl-1-piperazinyl]-1,4-dihydro-4-oxo-3-quinolinecarboxylic acid A 400 mg portion of 1-ethyl-6-fluoro-7-[3[(hexyloxy)-methyl]-1-piperazinyl]-1,4-dihydro-4-oxo-3-quinolinecarboxylic acid was added to a mixture of 1.2 ml of 37% formaldehyde and 1.5 ml of 90% formic acid. The mixture was heated on a steam bath for one hour, evaporated to an oil, diluted with 5 ml of water and neutralized with 1N sodium hydroxide. The solid was collected and dried, giving 360 mg of the desired product, mp 172°–174° C.

EXAMPLE 79

2-(3,5-Dimethyl-2-furanyl)piperazine

A 14.4 g portion of selenium dioxide was dissolved in 40 ml of dioxane and 7 ml of water with warming and stirring. A 14.5 g portion of 2-acetyl-3,5-dimethylfuran was added and the mixture was stirred at 80° C. for 4 hours. The mixture was filtered and the filtrate evaporated in vacuo to a gum. The gum was evaporated three times from toluene, then dissolved in 300 ml of ethanol. The filtrate was cooled to 0°–5° C. in an ice bath and 8 g of ethylenediamine in 50 ml of ethanol added dropwise. The mixture was stirred at room temperature for 18 hours, recooled in an ice bath and 9 g of sodium borohydride added. This mixture was stirred for 6 hours, quenched with water and evaporated to a gum. The gum was partitioned between dichloromethane and water, the organic layer separated, washed with water and evaporated to a gum. This gum was purified by chromatography, giving 1.4 g of 2-(3,5-dimethyl-2-furanyl)piperazine.

EXAMPLE 80

7-[3-(3,5-Dimethyl-2-furanyl)-1-piperazinyl]-6-fluoro-1,4-dihydro-4-oxo-3-quinolinecarboxylic acid The 1.4 g of 2-(3,5-dimethyl-2-furanyl)piperazine was dissolved in 5 ml of pyridine, 0.66 g of 1-ethyl-6,7-difluoro-1,4-dihydro-4-oxo-3-quinolinecarboxylic acid added and the mixture heated at 95°-100° C., under argon, in a pressure bottle for 4 hours, then cooled. The solvent was removed in vacuo, the residue evaporated twice from toluene and the residue chromatographed, giving 700 mg of crude product. This product was recrystallized from methanol, giving 220 mg of the desired product, mp 230°-232° C.

EXAMPLE 81

1-Cyclopropyl-6-fluoro-1,4-dihydro-7-[3-(methoxymethyl)-1-piperazinyl]-4-oxo-3-quinolinecarboxylic acid A mixture of 0.6 g of 7-chloro-1-cyclopropyl-6-fluoro-1,4-dihydro-4-oxo-3-quinolinecarboxylic acid and 1.4 g of 2-(methoxymethyl)piperazine in 4 ml of pyridine was heated at 120°-130° C. under argon in a pressure bottle for 18 hours. The solvent was removed and the residue was chromatographed and the crude product triturated with methanol and ether, giving 370 mg of the desired product as white crystals, mp 215°-216° C.

EXAMPLE 82

6-Fluoro-1-(4-fluorophenyl)-1,4-dihydro-7-(3-(methoxymethyl)-1-piperazinyl]-4-oxo-3-quinolinecarboxylic acid A 906 mg portion of 7-chloro-6-fluoro-1-(4-fluorophenyl)-1,4-dihydro-4-oxo-3-quinolinecarboxylic acid and 1.4 g of 2-(methoxymethyl)piperazine were added to 10 ml of pyridine and reacted as described in Example 81, giving 187 mg of the desired product, mp 216°-218° C.

EXAMPLE 83

1-Cyclopropyl-6-fluoro-1,4-dihydro-4-oxo-7-[3-(phenoxymethyl)-1-piperazinyl]-3-quinolinecarboxylic acid A 0.6 g portion of 7-chloro-1-cyclopropyl-6-fluoro-1,4-dihydro-4-oxo-3-quinolinecarboxylic acid, 1.23 g of 3-(phenoxymethyl)piperazine and 5 ml of pyridine were reacted as described in Example 81, giving 235 mg of the desired product, mp 112°-115° C.

EXAMPLE 84

1-(4-Fluorophenyl)-6-fluoro-1,4-dihydro-4-oxo-7-[3-(phenoxymethyl)-1-piperazinyl]-3-quinolinecarboxylic acid A mixture of 0.6 g of 7-chloro-6-fluoro-1-(4-fluorophenyl)-1,4-dihydro-4-oxo-3-quinolinecarboxylic acid, 1.03 g of 3-(phenoxymethyl)piperazine and 5 ml of pyridine was reacted as described in Example 81, giving 295 mg of the desired product, mp 204°-207° C.

EXAMPLE 85

1-Ethyl-5,6,8-trifluoro-1,4-dihydro-7-(4-methyl-1-piperazinyl)-4-oxo-3-quinolinecarboxylic acid A mixture of 65.5 g of 2,3,4,5-tetrafluoroaniline and 86.5 g of diethyl diethylethoxymethylene malonate was stirred and heated at 130° C. for one hour, then allowed to cool and the solid, which was [[(2,3,4,5-tetrafluorophenyl)amino]methylene], diethyl ester, collected. This solid was added to 400 ml of diphenyl ether, heated at 250° C. for one hour, then cooled, diluted with hexane and cooled in ice. The solid was collected, dried and recrystallized from dimethylformamide with charcoal treatment, giving 57.9 g of 5,6,7,8-tetrafluoro-4-hydroxy-3-quinolinecarboxylic acid, ethyl ester.

A mixture of 2.89 g of the above ester, 480 mg of hexane washed sodium hydride and 25 ml of dry dimethylformamide was stirred for 30 minutes. A 4 ml portion of ethyl iodide was added. The mixture was warmed slightly then stirred at room temperature for 18 hours. The mixture was poured into cold water and the solid collected. This solid was dissolved in dichloromethane, filtered and precipitated with hexane at the boil, giving 1-ethyl-5,5,6,7,8-tetrafluoro-1,4-dihydro-4-oxo-3-quinolinecarboxylic acid, ethyl ester.

A mixture of 4 g of the above ester, 50 ml of water and 50 ml of concentrated hydrochloric acid was heated at reflux for one hour, then cooled in ice and the solid collected, washed with water and dried, giving 3.26 g of 1-ethyl-5,6,7,8-tetrafluoro-1,4-dihydro-4-oxo-3-quinolinecarboxylic acid.

A 50 mg portion of the above acid was dissolved in a few drops of 1-methyl-2-pyrrolidinone with warming. A 43 mg portion of N-methylpiperazine was added and the mixture was allowed to stand for 2 hours. Ether was added, the solid collected and washed with ether and hexane. The solid was dissolved in acetone, treated with charcoal and precipitated with hexane at the boil, giving 34 mg of the desired product as light yellow crystals, mp 221°-223° C.

EXAMPLE 86

1-Ethyl-5,6,8-trifluoro-1,4-dihydro-7-(4-methyl-1-piperazinyl)-4-oxo-3-quinolinecarboxylic acid, monohydrochloride A 50 mg portion of 1-ethyl-5,6,8-trifluoro-1,4-dihydro-7-(4-methyl-1-piperazinyl)-4-oxo-3-quinolinecarboxylic acid was dissolved in 50 ml of dichloromethane and acidified with hydrochloric acid. Hexane and ether were added, the mixture was filtered and the solid which formed was collected, washed with ether, then hexane and dried, giving the desired salt, mp 271°-273° C.

EXAMPLE 87

1-Ethyl-5,6,8-trifluoro-1,4-dihydro-4-oxo-7-(1-pyrrolidinyl)-3-quinolinecarboxylic acid A 200 mg portion of 1-ethyl-5,6,7,8-tetrafluoro-1,4-dihydro-4-oxo-3-quinolinecarboxylic acid was dissolved in 1 ml of 1-methylpyrrolidine with warming. A 130 mg portion of pyrrolidine was added dropwise, the reaction was allowed to stand one hour and then diluted with ether. The solid was collected, washed with ether and hexane, dried and recrystallized from a mixture of dichloromethane-acetone, giving 140 mg of the desired product as white crystals, mp >320° C.

EXAMPLE 88

1-Ethyl-5,6,8-trifluoro-1,4-dihydro-7-(4-morpholinyl)-4-oxo-3-quinolinecarboxylic acid A mixture of 289 mg of 1-ethyl-5,6,7,8-tetrafluoro-1,4-dihydro-4-oxo-3-quinolinecarboxylic acid, 300 mg of morpholine and 5.6 ml of 1-methyl-2-pyrrolidone was heated in a stoppered flask at 65° C. for one hour. Ether was added, the solid collected, dissolved in 200 ml of acetone, filtered and boiled down to about 50 ml. The solid was collected, giving 137 mg of the desired product, mp 281°–283° C.

EXAMPLE 89

1-Ethyl-5,6,8-trifluoro-1,4-dihydro-4-oxo-7-(4-thiomorpholinyl)-3-quinolinecarboxylic acid A 289 mg portion of 1-ethyl-5,6,7,8-tetrafluoro-1,4-dihydro-4-oxo-3-quinolinecarboxylic acid was dissolved in 3 ml of 1-methyl-2-pyrrolidone. A 350 mg portion of thiomorpholine was added and the mixture was stirred for 2 hours. Ether was added, the solid collected and recrystallized from acetone, giving 250 mg of the desired product as a white solid, mp 308°–310° C.

EXAMPLE 90

1-Ethyl-5,6,8-trifluoro-1,4-dihydro-4-oxo-7-[3-(3-thienyl)-1-piperazinyl]-3-quinolinecarboxylic acid A 289 mg portion of 1-ethyl-5,6,7,8-tetrafluoro-1,4-dihydro-4-oxo-3-quinolinecarboxylic acid was dissolved in 3 ml of 1-methyl-2-pyrrolidone. A 500 mg portion of 3-thienyl piperazine was added, the mixture was stirred for 4 hours and then diluted with ether. After standing 2 hours, the solid was collected, washed with ether and hexane and recrystallized from acetone-hexane, giving 130 mg of the desired product as cream colored crystals, mp 221°–222° C.

EXAMPLE 91

1-Ethyl-5,6,8-trifluoro-1,4-dihydro-7-(3-methyl-1-piperazinyl)-4-oxo-3-quinolinecarboxylic acid A 289 mg portion of 1-ethyl-5,6,7,8-tetrafluoro-1,4-dihydro-4-oxo-3-quinolinecarboxylic acid was dissolved in 3 ml of 1-methyl-2-pyrrolidone. A 390 mg portion of 2-methyl piperazine was added, the mixture was stirred for 18 hours and then diluted with ether. The solid was collected, washed with hexane, dried and recrystallized from dichloromethane-acetone, giving 240 mg of solid. This solid was purified by chromatography, eluting with a gradient of chloroform-methanol-water and then a gradient of chloroform-methanol-water-acetic acid. The active fractions were combined and partitioned between dilute sodium bicarbonate and dichloromethane. The organic layer was dried and evaporated. The solid was recrystallized from dichloromethane-hexane, giving 100 mg of the desired product as off-white crystals, mp 220°–222° C.

EXAMPLE 92

1-Cyclopropyl-6-fluoro-1,4-dihydro-4-oxo-7-[3-(3-furanyl)-1-piperazinyl]-3-quinolinecarboxylic acid A mixture of 365 mg of 7-chloro-1-cyclopropyl-6-fluoro-1,4-dihydro-4-oxo-3-quinolinecarboxylic acid, 593 mg of 3-(3-furanyl)piperazine and 10 ml of pyridine was heated in a pressure bottle at about 120° C. for 2 days, then allowed to cool and the solvent removed. The residue was purified by flash silica gel column chormatography eluting with chloroform:methanol:water:triethylamine (95:5:1:1). This product was then triturated with methanol-ether and the solid, washed with methanol, then ether and dried in vacuo, giving 125 mg of the desired product, mp 202°–204° C.

EXAMPLE 93

3-(3-Furanyl)piperazine

To a solution of 6.25 ml of n-butyl lithium in ether at −78° C., under argon, was added 1.46 g of 3-bromofuran. The reaction was stirred at −78° C. for 30 minutes and then a solution of 1.13 g of N-acetyl-N,-O-dimethylhydroxyamine in ether was added. The mixture was stirred for an additional hour at −78° C., then raised to room temperature and quenched with dilute acid. The mixture was extracted several times with ether. The extracts were combined, dried and evaporated, giving 8.88 g of solid. A solution of this solid in 200 ml of dioxane was added to a mixture of 9.99 g of selenium dioxide, 1.62 ml of water and 200 ml of dioxane, which had been heated at 55° C. until a solution formed. This mixture was refluxed for 4 hours, then cooled and filtered through hydrous magnesium silicate. The filtrate was concentrated and purified by silica gel chromatography, eluting with hexane:ethyl acetate (4:1), giving 5.1 g of solid. To a solution of 4.544 g of this solid in 100 ml of ethanol at 0° C., under argon, was added dropwise a solution of 1.8 g of ethylene diamine in 20 ml of ethanol, followed by 10 ml of dioxane. This mixture was stirred at room temperature for 3-hours, then cooled to 0° C. and 2.42 g of sodium borohydride was added. This mixture was stirred at 0° C. for 2 hours, then quenched with water and evaporated. The residue was recrystallized from dichloromethane, giving 3.35 g of 3-(3-furanyl)piperazine.

EXAMPLE 94

1-Ethyl-6-fluoro-1,4-dihydro-4-oxo-7-[3-(3-furanyl)-1-piperazinyl]-3-quinolinecarboxylic acid A mixture of 592 mg of 3-(3-furanyl)piperazine, 329 mg of 1-ethyl-6,7-difluoro-1,4-dihydro-4-oxo-3-quinolinecarboxylic acid and 8 ml of pyridine was heated in a pressure bottle at 95°–100° C. for 18 hours and then purified as described in Example-65, giving 160 mg of the desired product, mp 202°–204° C.

EXAMPLE 95

7-(3-Cyclopropyl-1-piperazinyl)-1-ethyl-6-fluoro-1,4-dihydro-4-oxo-3-quinolinecarboxylic acid A mixture of 1.265 g of 1-ethyl-6,7-difluoro-1,4-dihydro-4-oxo-3-quinolinecarboxylic acid, 1.86 g of 3-cyclopropylpiperazine and 15 ml of pyridine was heated at 100° C. in a pressure bottle for 3 hours, then cooled and evaporated. The residue was purified by silica gel flash chromatography, eluting with chloroform:methanol:water:triethylamine (9:0.5:0.02:0.02), giving 180 mg of the desired product, mp 250° C. (dec.).

EXAMPLE 96

7-(3-Cyclopropyl-1-piperazinyl)-1-cyclopropyl-6-fluoro-1,4-dihydro-4-oxo-3-quinolinecarboxylic acid A mixture of 787 mg of 7-chloro-1-cyclopropyl-6-fluoro-1,4-dihydro-4-oxo-3-quinolinecarboxylic acid, 1.736 g of 3-cyclopropylpiperazine and 8 ml of pyridine was heated at 140° C. in a pressure bottle for 18 hours and then purified as described in Example 95, giving 182 mg of the desired product, mp 245° C. (dec.).

EXAMPLE 97

1-Cyclopropyl-6-fluoro-1,4-dihydro-4-oxo-7-[4-methyl-3-(2-furanyl)-1-piperazinyl]-3-quinolinecarboxylic acid A mixture of 200 mg of 1-cyclopropyl-6-fluoro-7-[3-(2-furanyl)-1-piperazinyl]-1,4-dihydro-4-oxo-3-quinolinecarboxylic acid, 0.3 ml of 90% formic acid and 0.24 ml of 37% formalin was heated for 2 hours, then evaporated. The residue was diluted with water, neutralized to pH 7 with 1N sodium hydroxide, the solid collected and washed with water, methanol and ether and dried in vacuo, giving 145 mg of the desired product, mp 122°-124° C.

EXAMPLE 98

1-Cyclopropyl-6-fluoro-1,4-dihydro-4-oxo-7-[3-(3-thienyl)-1-piperazinyl]-3-quinolinecarboxylic acid, monohydrochloride A 200 mg portion of 1-cyclopropyl-6-fluoro-1,4-dihydro-4-oxo-7-[3-(3-thienyl)-1-piperazinyl]-3-quinolinecarboxylic acid was dissolved in 2 ml of 1N sodium hydroxide, then 10% aqueous hydrochloric acid was added until the pH was 3. The mixture was stirred for 30 minutes, then the solid was collected and dried, giving 170 mg of the desired product.

EXAMPLE 99

1-Cyclopropyl-6-fluoro-1,4-dihydro-4-oxo-7-[3-(2-furanyl)-1-piperazinyl]-3-quinolinecarboxylic acid, monohydrochloride A 397 mg portion of 1-cyclopropyl-6-fluoro-7-[3-(2-furanyl)-1-piperazinyl]-1,4-dihydro-4-oxo-3-quinolinecarboxylic acid was reacted as described in Example 98, giving 158 mg of the desired product.

EXAMPLE 100

1,4-Dihydro-6-fluoro-1-(4-fluorophenyl)-4-oxo-7-[3-(3-thienyl)-1-piperazinyl]-3-quinolinecarboxylic acid A mixture of 670 mg of 7-chloro-6-fluoro-1-(4-fluorophenyl)-1,4-dihydro-4-oxo-3-quinolinecarboxylic acid, 1.34 g of 3-thienylpiperazine and 6 ml of pyridine was heated at 130°-140° C. for 24 hours, then cooled, triturated with ether and the solid collected, washed with methanol, ether and dried, giving 410 mg of the desired product, mp 246° C. (dec.).

EXAMPLE 101

7-(3-Ethenyl-1-piperazinyl)-1-ethyl-6-fluoro-1,4-dihydro-4-oxo-3-quinolinecarboxylic acid A mixture of 1.2 g of 1-ethyl-6,7-difluoro-1,4-dihydro-4-oxo-3-quinolinecarboxylic acid, 1.9 g of 3-ethenylpiperazine and 15 ml of pyridine is heated at 100° C. in a pressure bottle for 3 hours, then cooled and evaporated. The residue is purified by silica gel flash chromatography, eluting with chloroform:methanol:water:triethylamine (9:0.5:0.02:0.02), giving 200 mg of the desired product.

EXAMPLE 102

1-Cyclopropyl-7-(3-ethenyl-1-piperazinyl)-6-fluoro-1,4-dihydro-4-oxo-3-quinolinecarboxylic acid A mixture of 1.3 g of 7-chloro-1-cyclopropyl-6-fluoro-1,4-dihydro-4-oxo-3-quinolinecarboxylic acid, 1.9 g of 3-ethenylpiperazine and 15 ml of pyridine is heated at 140° C. in a pressure bottle for 18 hours and then purified as described in Example 101, giving 210 mg of the desired product.

EXAMPLE 103

1-Cyclopropyl-7-(3-ethenyl-4-methyl-1-piperazinyl)-6-fluoro-1,4-dihydro-4-oxo-3-quinolinecarboxylic acid A mixture of 200 mg of 1-cyclopropyl-7-(3-ethenyl-1-piperazinyl)-6-fluoro-1,4-dihydro-4-oxo-3-quinolinecarboxylic acid, 0.3 ml of 90% formic acid and 0.24 ml of 37% formalin is heated for 2 hours, then evaporated. The residue is diluted with water, neutralized to pH 7 with 1N sodium hydroxide, the solid collected, and washed with water, ether and dried in vacuo, giving 150 mg of the desired product.

EXAMPLE 104

1-Ethyl-7-(3-ethynyl-1-piperazinyl)-6-fluoro-1,4-dihydro-4-oxo-3-quinolinecarboxylic acid A mixture of 1.12 g of 1-ethyl-6,7-difluoro-1,4-dihydro-4-oxo-3-quinolinecarboxylic acid, 1.95 g of 3-ethynylpiperazine and 15 ml of pyridine is heated at 100° C. in a pressure bottle for 3 hours, then cooled and evaporated. The residue is purified by silica gel flash chromatography, eluting with chloroform:methanol:water:triethylamine (9:0.5:0.02:0.02), giving 200 mg of the desired product.

EXAMPLE 105

1-Cyclopropyl-7-(3-ethynyl-1-piperazinyl)-6-fluoro-1,4-dihydro-4-oxo-3-quinolinecarboxylic acid A mixture of 1.23 g of 7-chloro-1-cyclopropyl-6-fluoro-1,4-dihydro-4-oxo-3-quinolinecarboxylic acid, 1.95 g of 3-ethynylpiperazine and 15 ml of pyridine is heated at 140° C. in a pressure bottle for 18 hours and then purified as described in Example 101, giving 210 mg of the desired product.

EXAMPLE 106

1-Cyclopropyl-7-(3-ethynyl-4-methyl-1-piperazinyl)-6-fluoro-1,4-dihydro-4-oxo-3-quinolinecarboxylic acid A mixture of 200 mg of 1-cyclopropyl-7-(3-ethynyl-1-piperazinyl)-6-fluoro-1,4-dihydro-4-oxo-3-quinolinecarboxylic acid, 0.3 ml of 90% formic acid and 0.24 ml of 37% formalin is heated for 2 hours, then evaporated. The residue is diluted with water, nuetralized to pH 7 with 1N sodium hydroxide, the solid collected, and washed with water, ether and dried in vacuo, giving 156 mg of the desired product.

EXAMPLE 107

7-[3-(2-Benzofuranyl)-1-piperazinyl]-1-cyclopropyl-6-fluoro-1,4-dihydro-4-oxo-3-quinolinecarboxylic acid A 200 mg portion of 7-chloro-1-cyclopropyl-6-fluoro-1,4-dihydro-4-oxo-3-quinolinecarboxylic acid and 570 mg of 2-(2-benzofuranyl)piperazine in 4 ml of pyridine was purged briefly with argon, then sealed in a pressure bottle and heated with stirring at 130° C. for 20 hours. The reaction mixture was then dissolved in dichloromethane, evaporated in vacuo and vacuum pumped for a short period, giving 862 mg of residue. This residue was dissolved in 3 ml of chloroform and precipitated with ether. The precipitate was collected and washed with ether, giving 522 mg of solid. This solid was triturated with a small amount of cold methanol and the solid was collected and washed with ether. This solid was slurried several times with ether, then treated twice with a mixture of dichloromethane and methanol. The solid was collected and dried in vacuo, giving 38 mg of the desired product, mp 203°-206° C.

EXAMPLE 108

3-(1-Methyl-1H-pyrazol-3(and 5)-yl)piperazine

A 10 g portion of pyrazine methyl ketone was suspended in 4 ml of dimethylformamide and 16.3 ml of N,N-dimethylformamide dimethyl acetal was added. The mixture was heated at reflux for 18 hours, cooled and 7.65 g of solid collected.

A 7.5 portion of the above solid was suspended in 75 ml of ethanol and 2.63 ml of methyl hydrazine was added. The mixture was refluxed for 18 hours. The reaction mixture was separated by chromatography on silica gel using the system hexane:ethyl acetate (1:1). Cuts 2 and 3 were combined and rechromatographed using hexane:ethyl acetate (3:2), giving 3.68 g of 3-(1-methyl-1H-pyrazol-3-yl)pyrazine.

Cut 4 was rechromatographed in the same manner, giving 1.52 g of 3-(1-methyl-1H-pyrazol-5-yl)pyrazine.

A 1.76 g portion of 3-(1-methyl-1H-pyrazol-3-yl)pyrazine and 0.5 g of platinum oxide catalyst in 75 ml of methanol was hydrogenated for 18 hours. The catalyst was removed and the filtrate evaporated, giving 1.8 g of 3-(1-methyl-1H-pyrazol-3-yl)piperazine.

A 1.5 g portion of 3-(1-methyl-1H-pyrazol-5-yl)pyrazine was hydrogenated in the same manner, giving 1.6 g of 3-(1-methyl-1H-pyrazol-5-yl)piperazine.

EXAMPLE 109

1-Ethyl-6-fluoro-1,4-dihydro-7-[4-methyl-3-(1-methyl-1H-pyrazol-3-yl)-1-piperazinyl]-4-oxo-3-quinolinecarboxylic acid A 1.0 g portion of 3-(1-methyl-1H-pyrazol-3-yl)piperazine and 508 mg of 1-ethyl-6,7-difluoro-1,4-dihydro-4-oxo-3-quinolinecarboxylic acid were dissolved in 5 ml of pyridine and heated at 85°-95° C. for 18 hours, in a pressure bottle which had been evacuated and filled with argon. Methanol was added and the solid collected, giving 610 mg of 1-ethyl-6-fluoro-1,4-dihydro-7-[3-(1-methyl-1H-pyrazol-3-yl)-1-piperazinyl]-4-oxo-3-quinolinecarboxylic acid.

A 195 mg portion of the above compound was suspended in 1.5 ml of formic acid and 1 2 ml of 37% formaldehyde. The mixture was heated to solution on a steam bath, then evaporated to a gel. A 3 ml portion of water was added, then 1N sodium hydroxide was added dropwise until neutral. The solid was collected, washed with water and dried, giving 160 mg of the desired product.

EXAMPLE 110

1-Ethyl-6-fluoro-1,4-dihydro-7-[4-methyl-3-(1-methyl-1H-pyrazol-5-yl)-1-piperazinyl]-4-oxo-3-quinolinecarboxylic acid A 0.9 g portion of 3-(1-methyl-1H-pyrazol-5-yl)piperazine and 457 mg of 1-ethyl-6,7-difluoro-1,4-dihydro-4-oxo-3-quinolinecarboxylic acid were dissolved in pyridine in an evacuated and argon filled pressure bottle and heated at 90°-95° C. for 18 hours. The mixture was filtered, the filtrate concentrated in vacuo and chilled. The solid was purified by chromatography on silica gel giving 210 mg of 1-ethyl-6-fluoro-1,4-dihydro-7-[3-(1-methyl-1H-pyrazol-5-yl)-1-piperazinyl]-4-oxo-3-quinolinecarboxylic acid.

A 135 mg portion of the above compound in 1.5 ml of formic acid and 1.2 ml of 37% formaldehyde was heated on a steam bath for one hour and then evaporated. The residue was dissolved in 2 ml of water, neutralized with 1N sodium hydroxide, concentrated, the solid collected washed with water and dried, giving 101 mg of the desired compound.

EXAMPLE 111

1-Cyclopropyl-5,6,8-trifluoro-1,4-dihydro-7-(4-methyl-1-piperazinyl)-4-oxo-3-quinolinecarboxylic acid A 7.35 g portion of magnesium chips, 1.5 ml of carbon tetrachloride and 15 ml of absolute ethanol were added to a dry flask. A solution of 48.1 g of diethyl malonate in 30 ml of absolute ethanol and 120 ml of anhydrous ether was added dropwise over a one hour period. When addition was complete, the mixture was stirred at reflux for 3 hours then cooled to −10° C. with dry ice/acetone. A solution of 70 g of pentafluorobenzoyl chloride in 120 ml of ether was added over 2 hours, maintaining the temperature at not more than −5° C. The mixture was then stirred overnight at room temperature, partially evaporated, cooled in crushed ice and an ice cold solution of 7.5 ml of concentrated sulfuric acid in 300 ml of water was added at a rate such that the internal temperature did not go above 5° C. The mixture was extracted several times with ether, the extracts combined, washed with saturated sodium chloride, dried and concentrated, giving 106 g of (pentafluorobenzoyl)propanedioic acid, diethyl ester as a yellow oil.

A mixture of 69 g of the above ester, 500 ml of dioxane and dry ice was heated in an oil bath at 100° C. for 3 hours and then stirred overnight at room temperature. A 1.75 g portion of water was added and the mixture was heated at 80° C. overnight. Heating at 80° C. was continued with the addition of 1.72 g of water over 3 hours. The reaction mixture was then diluted with dichloromethane, dried, filtered and concentrated giving 55 g of yellow oil. This oil was vacuum distilled, giving 36.5 g of 2,3,4,5,6-pentafluoro-beta-oxobenzenepropanoic acid, ethyl ester as an oil.

A 10 g portion of 2,3,4,5,6-pentafluoro-beta-oxobenzenepropanoic acid, ethyl ester, 7.26 g of triethyl orthoformate and 8.85 g of acetic anhydride were mixed and heated in an oil bath at 120° C. for 5 hours under a drying tube, then evaporated to an oil. This oil was partitioned between ether and water. The ether layer was washed with water, dried and concentrated, giving 11.9 of a yellow oil.

The 11.9 g of oil was dissolved in 200 ml of absolute ethanol and then cooled in an ice bath. A 2.4 g portion of cyclopropylamine was then added and the mixture was stirred in the ice bath for 18 hours. The volatiles were removed at room temperature, giving 12.38 g of a cream colored solid.

A 2.54 g portion of 50% sodium hydride was washed with hexane and then added to 40 ml of dimethylformamide. While stirring, 12.3 g of the above solid in 40 ml of dimethylformamide was added dropwise over one hour. The reaction was poured onto crushed ice/water and then filtered. The solid was collected, washed with water, dried and recrystallized from dichloromethane, giving 8.1 g of 1-cyclopropyl-5,6,7,8-tetrafluoro-1,4-dihydro-4-oxo-3-quinolinecarboxylic acid, ethyl ester.

A mixture of 6.4 g of the above ester, 37 ml of glacial acetic acid, 27 ml of water and 4.5 ml of concentrated sulfuric acid was heated in an oil bath at 120° C. for 1.5 hours, then poured onto crushed ice and filtered. The solid was washed with water, dried and recrystallized from acetone/hexane with charcoal treatment, giving 2.5 g of solid.

A 1 g portion of this solid was dissolved in 5 ml of 1-methyl-2-pyrrolidinone and 0.8 g of N-methylpiperazine was added. The reaction was stirred for 1.5 hours and then diluted with ether. The solid was collected, washed with hexane and dried, giving 1.05 g of the desired product as a cream colored solid, mp 245° C.

EXAMPLE 112

7-[3-(Difluoromethyl)-1-piperazinyl]-1-ethyl-6,8-difluoro-1,4-dihydro-4-oxo-3-quinolinecarboxylic acid A mixture of 3.54 g of pyrazine carboxaldehyde and 5.63 g of diethylaminosulfurtrifluoride were reacted as described by W. J. Middeton, J. of Chemistry, 40, 577 (1975). The product was purified by chromatography, then hydrogenated at 20° C. under 50 psi hydrogen with 0.58 g of platinum oxide in methanol for 4 hours. The product was collected and purified by chromatography, giving 100 mg of 3-difluoromethylpiperazine.

The above 100 mg of 3-difluoromethylpiperazine and 200 mg of 1-ethyl-1,4-dihydro-6,7,8-trifluoro-4-oxo-3-quinolinecarboxylic acid in 5 ml of pyridine was stirred at 75° C. overnight, then cooled and the solvent removed in vacuo. The residue was triturated in a hot methanol/chloroform mixture and then purified by chromatography on silica gel, eluting with methanol:dichloromethane (5:95), giving 90 mg of the desired product, mp 212°–227° C. (dec.).

EXAMPLE 113

Racemic 1-Ethyl-6,8-difluoro-7-[3-(fluoromethyl)-4-methyl-1-piperazinyl]-1,4-dihydro-4-oxo-3-quinolinecarboxylic acid A mixture of 650 mg of 2-(fluoromethyl)piperazine, 500 mg of 1-ethyl-1,4-dihydro-6,7,8-trifluoro-4-oxo-3-quinolinecarboxylic acid and 5 ml of pyridine was stirred under nitrogen in a capped bottle at for 2.5 hours. The solvent was removed and the residue triturated with methanol. The solid was collected, washed twice with methanol and dried, giving 376 mg of racemic 1-ethyl-6,8-difluoro-7-[3-(fluoromethyl)-1-piperazinyl]-1,4-dihydro-4-oxo-3-quinolinecarboxylic acid.

A 175 mg portion of the above compound was reacted as previously described with 0.41 g of sodium acetate, 3 ml of formic acid and 3 ml of formaldehyde, giving 90 mg of the desired product, mp 208°–210° C. (dec.).

EXAMPLE 114

(−)-1-Ethyl-6,8-difluoro-7-[3-(fluoromethyl)-4-methyl-1-piperazinyl]-1,4-dihydro-4-oxo-3-quinolinecarboxylic acid A mixture of 150 mg of (−)-1-ethyl-6,8-difluoro-7-[3-(fluoromethyl)-1-piperazinyl]-1,4-dihydro-4-oxo-3-quinolinecarboxylic acid (Ex. 64) was reacted as described previously with 400 mg of sodium acetate, 3 ml of formic acid and 3 ml of formaldehyde, giving 110 mg of the desired product, mp 208°–210° C. (dec.).

EXAMPLE 115

(+)-1-Ethyl-6,8-difluoro-7-[3-(fluoromethyl)-4-methyl-1-piperazinyl]-1,4-dihydro-4-oxo-3-quinolinecarboxylic acid A 715 mg portion of (+)-1-ethyl-6,8-difluoro-7-[3-(fluoromethyl)-1-piperazinyl]-1,4-dihydro-4-oxo-3-quinolinecarboxylic acid (Ex. 65) was reacted as described previously with 400 mg of sodium acetate, 3 ml of formic acid and 3 ml of formaldehyde, giving 125 mg of the desired product, mp 208°–210° C. (dec.).

EXAMPLE 116

1-Ethyl-6,8-difluoro-1,4-dihydro-4-oxo-7-[3-(2-pyridinyl)-1-piperazinyl]-3-quinolinecarboxylic acid A solution of bromopyridine in 70 ml of tetrahydrofuran was added to 120 ml of a 1.67M hexane solution of n-butyl lithium at −70° C. This mixture was stirred at −70° C. for 0.5 hour, then 8.55 g of 2-chloropyrazine was added. Stirring was continued at −70° C. for 2 hours, then the reaction was quenched by the addition of water and stirring at 20° C. overnight. Purification by chromatography gave 1.3 g of solid which was then reduced at 50 psi hydrogen at 40° C. with 0.7 g palladium on carbon for 5 hours, giving 320 mg of 2-(2-pyridinyl)piperazine.

The 320 mg of 2-(2-pyridinyl)piperazine, 270 mg of 1-ethyl-1,4-dihydro-6,7,8-trifluoro-4-oxo-3-quinolinecarboxylic acid and 5 ml of pyridine were stirred at 70°–80° C. for 4 hours, then cooled and the pyridine removed in vacuo. The residue was taken up in methanol and then precipitated with ether. The solid was collected and dried, giving 275 mg of the desired product, mp 222°–224° C. (dec.).

EXAMPLE 117

7-[3-(1,1-Difluoroethyl)-1-piperazinyl]-1-ethyl-6,8-difluoro-1,4-dihydro-4-oxo-3-quinolinecarboxylic acid A 4.3 g portion of 3-(1,1-difluoroethyl)pyrazine in 25 ml of methanol was reduced with 50 psi hydrogen and 750 mg of platinum oxide at 20° C. for 5 hours. The resulting oil was purified by chromatography, giving about 700 mg of 3-(1,1-difluoroethyl)piperazine.

The above compound was reacted with 360 mg of 1-ethyl-1,4-dihydro-6,7,8-trifluoro-4-oxo-3-quinolinecarboxylic acid in 6 ml of pyridine under nitrogen at 75° C. for 1.5 hours. A 70 mg portion of the acid was added and the reaction continued for 3 hours. The solvent was removed in vacuo and the residue triturated with dichloromethane, giving the desired product.

EXAMPLE 118

1-Cyclopropyl-6-fluoro-1,4-dihydro-4-oxo-7-[3-(3-pyridinyl)-1-piperazinyl]-3-quinolinecarboxylic acid To a solution of 12.1 g of 3-acetylpyridine in 100 ml of carbon tetrachloride at was added a solution of 15.9 g of bromine in 50 ml of carbon tetrachloride. After a few minutes the solvent was decanted and the residue triturated with a minimum amount of methanol, giving 3.906 g of solid.

This solid was added portionwise to 15 ml of ethylenediamine at 8°–10° C. When addition was complete, the reaction was allowed to warm to room temperature and stirred for 16 hours. The excess ethylenediamine was removed under reduced pressure. The crude product was dissolved in water, extracted several times with chloroform, then dried and the solvent evaporated, giving 1.932 g of solid.

This 1.932 g of solid was dissolved in 10 ml of ethanol, cooled to and 454 mg of sodium borohydride added. The mixture was stirred at 0° C. for one hour then the ethanol was removed and water added. The mixture was extracted with chloroform, dried, the solvent removed and the residue purified by flash silica gel chromatography using the system chloroform:methanol:water:triethylamine (9:0.5:0.01:0.01), giving 350 mg of 2-(3-pyridinyl)piperazine.

A mixture of 733.5 mg of 2-(3-pyridinyl)piperazine, 421.5 mg of 7-chloro-1-cyclopropyl-6-fluoro-1,4-dihydro-4-oxo-3-quinolinecarboxylic acid and 10 ml of pyridine was heated at 135° C. for 24 hours. The solvent was removed and the residue purified by chromatography on silica gel using chloroform:methanol:triethylamine:water (9.5:0.5:0.01:0.01), giving 120 mg of the desired product.

EXAMPLE 119

1-Cyclopropyl-6-fluoro-1,4-dihydro-4-oxo-7-[3-(1H-pyrrol-3-yl)-1-piperazinyl]-3-quinolinecarboxylic acid A mixture of 337 mg of 7-chloro-1-cyclopropyl-6-fluoro-1,4-dihydro-4-oxo-3-quinolinecarboxylic acid, 1.2 g of 1-(phenylsulfonyl)-3-(2-piperazinyl)-1H-pyrrole and 5 ml of pyridine was heated in a pressure bottle at 135° C. for 16 hours, then allowed to cool and the pyridine removed under reduced pressure. The crude substance was purified by column chromatography using chloroform:methanol:water:triethylamine (9:0.5:0.01:0.01), giving 270 mg of 1-cyclopropyl-6-fluoro-1,4-dihydro-4-oxo-7-[3-[1-(phenylsulfonyl)-1H-pyrrol-3-yl]-1-piperazinyl]-3-quinolinecarboxylic acid.

A mixture of 214 mg of the above compound in 3 ml of 1N sodium hydroxide and 10 ml of dioxane was heated at 100° C. for 4 hours, cooled, neutralized to pH 7 with 10% acetic acid and the solvents removed. The residue was collected and washed with water, methanol and ether, giving 136 mg of the desired product.

EXAMPLE 120

1-Ethyl-6-fluoro-1,4-dihydro-7-[4-methyl-2-(3-thienyl)-1-piperazinyl]-4-oxo-3-quinolinecarboxylic acid A solution of 1.20 g of 3-(3-thienyl)-1-piperazine carboxylic acid, ethyl ester in 100 ml of ether was added to a suspension of 380 mg of lithium aluminum hydride in 50 ml of ether. The mixture was refluxed for 12 hours and the product recovered, giving 850 mg of 4-methyl-2-(3-thienyl)piperazine.

A solution of 6 g of borontrifluoro etherate in 10 ml of anhydrous acetonitrile was added dropwise to a boiling mixture of 1.467 g of 1-ethyl-6,7-difluoro-1,4-dihydro-4-oxo-3-quinolinecarboxylic acid and 50 mg of 1,4-diazabicyclo(2.2.2)octane in 10 ml of anhydrous acetonitrile. When addition was complete the mixture was stirred at reflux temperature for 40 minutes, then the solvent was removed Aqueous sodium bicarbonate was added to pH 7, then the solid was collected, washed with water, ice-cold acetone and ether and dried, giving 1.516 g of (1-ethyl-6,7-difluoro-1,4-dihydro-4-oxo-3-quinolinecarboxylato-$O^3,O^4$)difluoroboron.

A mixture of 126 mg of the above boron derivative, 230 mg of 4-methyl-2-(3-thienyl)piperazine and 3 ml of dimethyl sulfoxide was stirred for 24 hours, then poured slowly into water and the solid collected, giving 150 mg of [1-ethyl-6-fluoro-1,4-dihydro-7-[4-methyl-2-(3-thienyl)-1-piperazinyl]-4-oxo-3-quinolinecarboxylato-$O^3,O^4$]difluoroboron.

A mixture of 50 mg of this solid, 0.4 ml of dimethylformamide, 0.4 ml of triethylamine and 4 ml of ethanol was heated at reflux for 16 hours, then the solvents were removed under reduced pressure. The residue was triturated with methanol and ether, the solid collected and recrystallized from chloroform/methanol/dimethylformamide, giving 29 mg of the desired product.

EXAMPLE 121

1-Cyclopropyl-6-fluoro-1,4-dihydro-4-oxo-7-[3-(1H-pyrazol-3-yl)-1-piperazinyl]-3-quinolinecarboxylic acid A mixture of 496 mg of 3-dimethylamino-1-(2-pyrazinyl)-2-propen-1-one and 10 ml of hydrazine hydrate was heated at 90°–100° C. for 16 hours, then allowed to cool, giving 210 mg of 1H-pyrazol-3-yl-pyrazine.

A mixture of 100 mg of the above compound, 100 mg of platinum oxide and 30 ml of methanol was hydrogenated in a Parr shaker for 5 hours. The mixture was filtered and the filtrate evaporated, giving 110 mg of 2-(1H-pyrazol-3-yl)piperazine.

A mixture of 703 mg of 7-chloro-1-cyclopropyl-6-fluoro-1,4-dihydro-4-oxo-3-quinolinecarboxylic acid, 1.14 g of 2-(1H-pyrazol-3-yl)piperazine and 5 ml of pyridine was heated in a pressure bottle at 130° C. for 24 hours. It was allowed to cool at room temperature, then cooled to 0° C., the pyridine removed and the crude product purified by flash chromatography on silica gel, giving 195 mg of the desired product.

EXAMPLE 122

1-Ethyl-6-fluoro-1,4-dihydro-4-oxo-7-[3-(3-pyridinyl)-1-piperazinyl]-3-quinolinecarboxylic acid A mixture of 177 mg of 1-ethyl-6,7-difluoro-1,4-dihydro-4-oxo-3-quinolinecarboxylic acid, 342 mg of 2-(3-pyridinyl)piperazine and 5 ml of pyridine was heated at 90°–95° C. in a pressure bottle for 5 hours, then cooled at room temperature, then at 0° C. Ether was added to triturate the mixture, then the solid was collected and washed with methanol and ether. This solid was redissolved in a hot mixture of chloroform and methanol, filtered and triturated with ether. The precipitate was collected and dried in vacuo, giving 110 mg of the desired product.

EXAMPLE 123

1-Ethyl-6-fluoro-1,4-dihydro-4-oxo-7-[3-(4-pyridinyl)-1-piperazinyl-3-quinolinecarboxylic acid To an 80° C. solution of 26.14 g of 4-acetylpyridine in 200 ml of carbon tetrachloride was added dropwise a solution of 34.43 g of bromine in 200 ml of carbon tetrachloride. The reaction was heated until decolorized, then cooled and the solvent decanted. The solid was broken into small pieces, suspended in methanol, filtered and washed with methanol and ether giving 17.2 g of solid.

To a solution of 35 g of ethylenediamine at 8°–10° C., under argon, was added 15.07 g of the above solid in small portions. When addition was complete the temperature was allowed to rise slowly to room temperature and the mixture was then stirred for 24 hours. Excess ethylenediamine was removed under reduced pressure, a little water was added to the residue, which was then extracted with chloroform, dried and the solvent removed. This solid was dissolved in 200 ml of ethanol, cooled to 0° C., 54 mg of sodium borohydride added, stirred at 0° C. for one hour, then at room temperature for one hour, quenched with water and the ethanol removed. The crude solid was partitioned between water and chloroform. The aqueous layer was extracted several times with chloroform. All the chloroform layers were combined, dried and evaporated. The residue was purified by flash chromatography on silica gel using chloroform:methanol:water:triethylamine (9:0.5:0.01:0.01), giving 1.3 g of 2-(4-pyridinyl)piperazine.

A mixture of 506 mg of 1-ethyl-6,7-difluoro-1,4-dihydro-4-oxo-3-quinolinecarboxylic acid, 1.3 g of 2-(4-pyridinyl)piperazine and 5 ml of pyridine was heated at 90°–95° C. for 4 hours in a pressure bottle. The pyridine was removed under reduced pressure and the residue triturated with a mixture of methanol and ether. The solid was collected, washed with methanol and ether and purified by the same chromatography as above, giving 140 mg of the desired product.

EXAMPLE 124

1-Cyclopropyl-7-(3-cyclopropyl-1-piperazinyl)-6-fluoro-1,4-dihydro-4-oxo-3-quinolinecarboxylic acid, monohydrochloride A mixture of 1.405 g of 7-chloro-1-cyclopropyl-6-fluoro-1,4-dihydro-4-oxo-3-quinolinecarboxylic acid, 4.34 g of 2-cyclopropylpiperazine and 15 ml of pyridine was heated in a pressure bottle at 135° C. for 24 hours, then cooled and the pyridine removed under reduced pressure. The residue was purified by chromatography on silica gel, with chloroform:methanol:water:triethylamine (9.5:0.5:0.01:0.01). The solid (base form) was redissolved in ethanol, a few drops of concentrated hydrochloric acid were added and the solid collected, washed with cold ethanol, ether and dried, giving the desired products.

EXAMPLE 125

1-Cyclopropyl-7-(3-cyclopropyl-4-methyl-1-piperazinyl)-6-fluoro-1,4-dihydro-4-oxo-3-quinolinecarboxylic acid A mixture of 210 mg of 1-cyclopropyl-7-(3-cyclopropyl-1-piperazinyl)-6-fluoro-1,4-dihydro-4-oxo-3-quinolinecarboxylic acid, 0.24 ml of 37% formaldehyde and 0.30 ml of 90% formic acid was heated at 100° C. for 4 hours, then allowed to cool and the excess reagents removed under reduced pressure. Water was added and the pH adjusted to 7 with 1N sodium hydroxide. The mixture was then extracted several times with chloroform:methanol (95:5), the extracts combined, dried, filtered and evaporated. The resulting oil was triturated with ether, giving 170 mg of the desired product.

EXAMPLE 126

1-Cyclopropyl-6-fluoro-1,4-dihydro-4-oxo-7-[3-(4-pyridinyl)-1-piperazinyl]-3-quinolinecarboxylic acid, monohydrochloride A solution of 12.347 g of borontrifluoro etherate in 40 ml of anhydrous acetonitrile was added dropwise to a boiling mixture of 3.5 g of 7-chloro-1-cyclopropyl-6-fluoro-1,4-dihydro-4-oxo-3-quinolinecarboxylic acid and 150 mg of 1,4-diazabicyclo(2.2.2)octane in 40 ml of acetonitrile. When addition was complete, the mixture was stirred at reflux for an additional 40 minutes, then the solvent was removed and aqueous sodium bicarbonate added to pH 7. The solid was collected, washed with water, ice cold acetone and ether and dried, giving 3.55 g of (1-cyclopropyl 7 chloro 6 fluoro 1,4 dihydro 4 oxo 3 quinolinecarboxylato-$O^3,O^4$)difluoroboron.

A mixture of 300 mg of the above compound, 440 mg of 2-(4-pyridinyl)piperazine and 2 ml of dimethyl sulfoxide was stirred for 24 hours and then poured slowly into water. The solid was collected and dried, giving 250 mg of [1-cyclopropyl-6-fluoro-1,4-dihydro-4-oxo-7-[3-(4-pyridinyl)-1-piperazinyl]-3-quinolinecarboxylato-$O^3,O^4$]difluoroboron.

A mixture of 170 mg of the above compound, 0.2 ml of triethylamine, 3 ml of dimethylformamide and 5 ml of ethanol was refluxed for 3 hours, then cooled and the solvent removed. The solid was triturated with methanol and ether and then recrystallized from methanol and chloroform, giving 110 mg of the desired product.

EXAMPLE 127

1-Ethyl-6,8-difluoro-1,4-dihydro-4-oxo-7-[3-(4-pyridinyl)-1-piperazinyl]-3-quinolinecarboxylic acid A solution of 1.06 g of borontrifluoro etherate in 25 ml of anhydrous acetonitrile was added dropwise to a boiling mixture of 2.71 g of 1-ethyl-6,7,8-trifluoro-1,4-dihydro-4-oxo-3-quinolinecarboxylic acid and 50 mg of 1,4-diazabicyclo(2.2.2)octane in 25 ml of acetonitrile. When addition was complete, the mixture was stirred at reflux temperature for 40 minutes, then the solvent was removed and aqueous sodium bicarbonate added to pH 7. The solid was collected, washed with water, ice cold acetone and ether and dried, giving 2.8 g of (1-ethyl-6,7,8-trifluoro-1,4-dihydro-4-oxo-3-quinolinecarboxylato-$O^3,O^4$)difluoroboron.

A mixture of 223 mg of the above compound, 342 mg of 2-(4-pyridinyl)piperazine and 5 ml of dimethyl sulfoxide was stirred for 24 hours and then poured into water. The solid was collected and dried, then added to 1 ml of dimethylformamide, 1 ml of triethylamine and 10 ml of ethanol. This mixture was refluxed for 2 hours, the solvents removed, ethanol added, the solid collected and recrystallized from dimethylformamide/methanol, giving 100 mg of the desired product.

EXAMPLE 128

1-Cyclopropyl-6-fluoro-1,4-dihydro-4-oxo-7-[3-(2-pyridinyl)-1-piperazinyl]-3-quinolinecarboxylic acid A mixture of 1.316 g of (1-cyclopropyl-7-chloro-6-fluoro-1,4-dihydro-4-oxo-3-quinolinecarboxylato-$O^3,O^4$)difluoroboron, 1.956 g of 2-(2-pyridinyl)piperazine and 10 ml of dimethyl sulfoxide was stirred for 16 hours and then poured into water. The solid was collected and dried, giving 1.65 g of [1-cyclopropyl-6-fluoro-1,4-dihydro-4-oxo-7-[3-(2-pyridinyl)-1-piperazinyl]-3-quinolinecarboxylato-$O^3,O^4$)difluoroboron.

A 1.6 g portion of the above compound was dissolved in 30 ml of dimethylformamide and 2 ml of triethylamine and 10 ml of ethanol were added. This mixture was refluxed for 18 hours, the solvents removed under reduced pressure and the solid triturated with methanol, giving 1.2 g of the desired product.

EXAMPLE 129

1-Cyclopropyl-6-fluoro-1,4-dihydro-4-oxo-7-[3-(2-pyridinyl)-1-piperazinyl]-3-quinolinecarboxylic acid, monohydrochloride A 54 mg portion of the base compound from Example 128 was dissolved, with heat, in a mixture of ethanol, chloroform and a little dimethylformamide. A few drops of concentrated hydrochloric acid were added, the solid was collected, washed with water, ether and dried, giving 35 mg of the desired product.

EXAMPLE 130

1-Cyclopropyl-6,7-difluoro-1,4-dihydro-4-oxo-3-quinolinecarboxylic acid

A solution of 32 g of 2,4,5-trifluorobenzoic acid in 305 ml of ether, containing 5 drops of dimethylformamide was first evacuated and then purged with argon. A 27 ml portion of oxalyl chloride was added dropwise, using an addition funnel over a period of 30 minutes, while keeping the reaction under argon. When addition was complete, the mixture was stirred under argon for 30 minutes, then the ether was removed and the residual oil distilled at 0.2–1.0 mm, 28°–33° C., giving 30.9 g of 2,4,5-trifluorobenzoyl chloride as an oil.

A reaction mixture of 2.4 g of magnesium turnings, 360 ml of anhydrous ethanol and 5 ml of carbon tetrachloride was first evacuated, then purged with argon. A 16 g portion of diethyl malonate was added dropwise through an addition funnel. The mixture was stirred for one hour with a condenser because of an exotherm. The mixture was then heated at reflux for 2 hours followed by cooling to −10° C. A −10° C. solution of 19.45 g of 2,4,5-trifluorobenzoyl chloride in 20 ml of ether was added through an addition funnel. The mixture was stirred at −10° C. for one hour, then overnight at room temperature and then poured into 300 ml of ice/water. The pH was adjusted to 2.5 with concentrated sulfuric acid. The resulting suspension was concentrated to about 250 ml and extracted with chloroform. The extract was washed with water, dried, evaporated to an oil and distilled, giving 24.94 g of (2,4,5-trifluorobenzoyl)propanedioic acid, diethyl ester.

A solution of 23.8 g of (2,4,5-trifluorobenzoyl)propanedioic acid, diethyl ester, 2.7 ml of water and 740 ml of p-dioxane was placed in an oil bath and stirred at 102° C. for 7 hours. The solution was then evaporated to dryness, heptane was added and the mixture refrigerated overnight. The resulting crystals were collected, washed with 10 ml of cold heptane and dried, giving 10.8 g of 2,4,5-trifluoro-$\beta$-oxobenzenepropanoic acid, ethyl ester.

A solution of 7.88 g of 2,4,5-trifluoro-$\beta$-oxobenzenepropanoic acid, ethyl ester, 8.15 ml of 98% triethoxymethane and 7.5 ml of acetic anhydride in a 50 ml of flask was connected through a short distillation head to a 160 mm vacuum source and heated at 115° C. for 3 hours. The solution was then evaporated in vacuo at 45° C. giving 9.67 g of $\alpha$-(ethoxymethylene)-2,4,5-trifluoro-$\beta$-oxobenzenepropanoic acid, ethyl ester as a yellow oil.

A solution of 9.67 g of $\alpha$-(ethoxymethylene)-2,4,5-trifluoro-$\beta$-oxobenzenepropanoic acid, ethyl ester in 70 ml of dry ether was cooled in an ice bath to 10° C. A 2.44 ml portion of cyclopropylamine was added dropwise, maintaining the reaction temperature at 10 to 11° C. When addition was complete the ice bath was removed, the mixture stirred at room temperature for 10 minutes and then evaporated, giving 10.02 g of $\alpha$-[(cyclopropylamino)methylene]2,4,5-trifluoro-$\beta$-oxobenzenepropanoic acid, ethyl ester as an oil.

A mixture of 10.02 g of $\alpha$-[(cyclopropylamino)methylene]-2,4,5-trifluoro-$\beta$-oxobenzenepropanoic acid, ethyl ester, 13.27 g of anhydrous potassium carbonate and 360 ml of dry dimethylformamide was stirred and heated at 50° C. for 5.0 hours, then filtered. The filtrate was cooled in an ice bath for one hour and the resulting crystals collected by filtration, washed with ether and dried giving 2.6 g (A). The filtrate was evaporated in vacuo giving 792 mg of crystals (B) which were collected by filtration. This filtrate was evaporated to an oily suspension, refrigerated 48 hours, dissolved in 150 ml of dimethylformamide, 7 g of potassium carbonate added and the suspension heated at 50° C. for 5 hours. The suspension was filtered, the filtrate cooled in an ice bath and the resulting crystals collected by filtration giving 1.66 g of crystals (C). The filtrate was evaporated to dryness and the residue recrystallized from chloroform, giving 2.6 g of crystals (D). Crystals (A), (B), (C) and (D) were combined and recrystallized from 35 ml of chloroform, with cooling in an ice bath, giving 6.12 g of 1-cyclopropyl-6,7-difluoro-1,4-dihydro-4-oxo-3-quinolinecarboxylic acid, ethyl ester.

A suspension of 7.85 g of 1-cyclopropyl-6,7-difluoro-1,4-dihydro-4-oxo-3-quinolinecarboxylic acid, ethyl ester in 220 ml of 2N sulfuric acid was heated at 100° C. overnight, then cooled in an ice bath. The solid was collected, washed with water and dried, giving 6.81 g of the desired compound, mp 292°–293° C.

EXAMPLE 131

1-Cyclopropyl-6-fluoro-7-[3-(fluoromethyl)-1-piperazinyl]-1,4-dihydro-4-oxo-3-quinolinecarboxylic acid A suspension of 530.4 mg of 1-cyclopropyl-6,7-difluoro-1,4-dihydro-4-oxo-3-quinolinecarboxylic acid, 90.7 mg of 2-(fluoromethyl)piperazine and 2 ml of pyridine was heated at 115° C. for 30 minutes, then filtered and the filtrate refrigerated overnight. The resulting crystals were collected, washed with water, ether and dried, giving 262 mg of the desired compound as light yellow crystals, mp 202°–203° C.

EXAMPLE 132

2-(Difluoromethyl)piperazine

2-Pyrazinecarboxaldehyde was prepared by the method of H. Rutner and P. E. Spoerri, J. Org. Chem., 28, 1898 (1963).

A 3.54 g portion of 2-pyrazinecarboxaldehyde in dichloromethane was stirred at −70° C. under a water free atmosphere. To this was added 5.63 g (4.3 ml) of diethylaminosulfurtrifluoride dropwise. The solution was allowed to warm to room temperature, then stirred overnight, filtered through Florisil (exotherm) and chromatographed on a column of silica gel, eluting with ether:hexane (1:1). The solvent was evaporated and the residue hydrogenated at 20° C. under 50 psi hydrogen with 0.58 g of platinum oxide catalyst in methanol in a Parr shaker for 4 hours. The mixture was filtered through diatomaceous earth. The filtrate was chromatographed on alumina, eluting with ether, then dichloromethane:ether (1:1), then dichloromethane and finally 5% methanol in dichloromethane, giving 100 mg of the desired compound as hygroscopic crystals.

EXAMPLE 133

1-Cyclopropyl-6-fluoro-7-[3-(difluoromethyl)-1-piperazinyl-[-1,4-dihydro-4-oxo-3-quinolinecarboxylic acid Following the procedure of Example 131, but using 2-(difluoromethyl)piperazine in place of 2-(fluoromethyl)piperazine, the desired product is obtained.

EXAMPLE 134

2-(Trifluoromethyl)piperazine

A 12.3 g portion of bromo-3,3,3-trifluoropropanone was slowly added to 50 ml of dimethyl sulfoxide and stirred under a dry atmosphere for 21 hours and then diluted to 100 ml with ethanol. A solution of 31 g of N,N-dibenzylethylenediamine in 100 ml of ethanol was added dropwise and the mixture was stirred for 8 hours. A 2.43 g portion of sodium borohydride was added over 30 minutes, this mixture was stirred overnight then the ethanol was removed. The dimethyl sulfoxide residue was dissolved in water and extracted with dichloromethane. The extracts were combined, washed with water and brine and then subjected to flash chromatography on a silica gel column, eluting with ether:hexane (3:7). The 2-(trifluoromethyl)dibenzylpiperazine was dissolved in 25 ml of ethanol in an argon flushed Parr bottle. A 0.63 g portion of 10% palladium on carbon was added and the mixture was shaken under 47 lbs. of hydrogen pressure overnight at 40° C. Filtration and evaporation of the solvent gave 0.55 g of 2-(trifluoromethyl)piperazine as a semi-solid.

EXAMPLE 135

1-Cyclopropyl-6-fluoro-7-[3-(trifluoromethyl)-1-piperazinyl-[-1,4-dihydro-4-oxo-3-quuinolinecarboxylic acid A 0.55 g portion of 2-(trifluoromethyl)piperazine was dissolved in 14 ml of pyridine. To this was added 265 mg of 1-cyclopropyl-6,7-difluoro-1,4-dihydro-4-oxo-3-quinolinecarboxylic acid. The mixture was stirred for 3 hours at 77° C. The pyridine was removed by repeated evaporation with toluene. The residue was triturated with hot methanol. The resulting solid was collected, washed with methanol and ether and dried, giving 105 mg of the desired product as a colorless solid.

What is claimed is:

1. A compound of the formula:

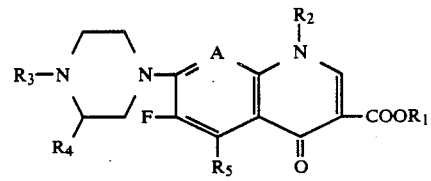

wherein $R_1$ is hydrogen, alkyl($C_1$–$C_3$), dialkyl($C_1$–$C_3$)aminoalkyl($C_1$–$C_3$), N-piperidinoalkyl($C_1$–$C_3$), N-morpholinoalkyl($C_1$–$C_3$), N-4-methylpiperidinoalkyl($C_1$–$C_3$), 3-substituted-N-piperazinyl, N-4-alkyl($C_1$–$C_3$)piperazinylalkyl($C_1$–$C_3$), $R_7$ —CH—$OR_6$ where $R_6$ is acyl or $COOR_8$, $R_8$ is alkyl($C_1$–$C_3$) and $R_7$ is hydrogen or alkyl($C_1$–$C_3$), or an alkali or alkaline earth metal; $R_2$ is alkyl($C_1$–$C_4$), cycloalkyl($C_3$–$C_6$), alkoxy($C_1$–$C_4$), alkylamino($C_1$–$C_3$), vinyl phenyl, benzyl, —$CH_2CH_2F$ or mono- or polysubstituted phenyl (wherein the substituent is halogen, $CF_3$ or $OCH_2F$); $R_3$ is hydrogen, benzyl, or alkyl($C_1$–$C_3$); $R_4$ is fluoromethyl, difluoromethyl, trifluoromethyl, cyclopropyl, ethenyl, ethynyl, 5 or 6-membered ring heteroaryl or substituted heteroaryl having at least one —O—, —N—, or —S—, that is not 2-furanyl or 2-theinyl; $R_5$ is hydrogen or fluoro; A is =N—, =CH—, or =CF—; and when $R_1$ is hydrogen, the pharmacologically acceptable salts thereof.

2. A compound according to claim 1, which is selected from the group consisting of (racemic)-N-ethyl-6,8-difluoro-7-[(3-fluoromethyl)-1-piperazinyl]-1,4-dihydro-4-oxo-3-quinolinecarboxylic acid; 7-(3-cyclopropyl-1-piperazinyl)-1-ethyl-6-fluoro-1, 4-dihydro-4-oxo-3-quinolinecarboxylic acid; and 7-(3-cyclopropyl-1-piperazinyl)-1-cyclopropyl-6-fluoro-1,4-dihydro-4-oxo-3-quinolinecarboxylic acid.

3. A compound according to claim 1 which is selected from the group consisting of: 7-[3-(2-benzofuranyl)-1-piperazinyl]-1-cyclopropyl-6-fluoro-1,4-dihydro-3-quinolinecarboxylic acid; 1-ethyl-6-fluoro-1,4-dihydro-7-[4-methyl-3-(1-methyl-1H-pyrazol-3-yl)-1-piperazinyl]-4-oxo-3-quinoline; and racemic 1-ethyl-6,8-difluoro-7-[3-(fluoromethyl)-4-methyl-1-piperazinyl]-1,4-dihydro-4-oxo-3-quinolinecarboxylic acid.

4. A method of treating bacterial infections in warm-blooded animals which comprises administering to said animals an antibacterially effective amount of a compound selected from those of claims 1 and 2.

5. A composition of matter in dosage unit form comprising from 100 to 750 mg of a compound selected from those of claims 1 and 2 in association with a pharmaceutically acceptable carrier.

6. A compound according to claim 1 which is selected from the group consisting of: 1-ethyl-6-fluoro-1,4-dihydro-7-[4-methyl-3-(1-methyl-1H-pyrazol-5-yl)-1-piperazinyl]-4-oxo-3-quinolinecarboxylic acid; 7-[3-(difluoromethyl)-1-piperazinyl]-1-ethyl-6,8-difluoro-1,4-dihydro-4-oxo-3-quinolinecarboxylic acid; (−)-1-ethyl-6,8-difluoro-7-[3-(fluoromethyl)-4-methyl-1-piperazinyl]-1,4-dihydro-4-oxo-3-quinolinecarboxylic acid; (+)-1-ethyl-6,8-difluoro-7-[3-(fluoromethyl)-4-methyl-1-piperazinyl]-1,4-dihydro-4-oxo-3-quinolinecarboxylic acid; 1-ethyl-6,8-difluoro-1,4-dihydro-4-oxo-7-[3-(2-pyridinyl)-1-piperazinyl]-3-quinolinecarboxylic acid; 7-[3-(1,1-difluoroethyl)-1-piperazinyl]-1-ethyl-6,8-difluoro-1,4-dihydro-4-oxo-3-quinolinecarboxylic acid; 1-cyclopropyl-6-fluoro-1,4-dihydro-4-oxo-7-[3-pyridinyl)-1-piperazinyl]-3-quinolinecarboxylic acid; 1-cyclopropyl-6-fluoro-1,4-dihydro-4-oxo-7-[3-(1H-pyrrol-3-yl)-1-piperazinyl]-3-quinolinecarboxylic acid; 1-ethyl-6-fluoro-1,4-dihydro-7-[4-methyl-2-(3-thienyl)-1-piperazinyl]-4-oxo-3-quinolinecarboxylic acid; 1-cyclopropyl-6-fluoro-1,4-dihydro-4-oxo-7-[3-(1H-pyrazol-3-yl)-1-piperazinyl]-3-quinolinecarboxylic acid; 1-ethyl-6-fluoro-1,4-dihydro-4-oxo-7-[3-(3-pyridinyl)-1-piperazinyl)-3-quinolinecarboxylic acid; 1-ethyl-6-fluoro-1,4-dihydro-4-oxo-7-[3-(4-pyridinyl)-1-piperazinyl-3-quinolinecarboxylic acid; 1-cyclopropyl-7-(3-cyclopropyl-1-piperazinyl)-6-fluoro-1,4-dihydro-4-oxo-3-quinolinecarboxylic acid, monohydrochloride; 1-cyclopropyl-7-(3-cyclopropyl-4-methyl-1-piperazinyl)-6-fluoro-1,4-dihydro-4-oxo-3-quinolinecarboxylic acid; 1-cyclopropyl-6-fluoro-1,4-dihydro-4-oxo-7-[3-(4-pyridinyl)-1-piperazinyl]-3-quinolinecarboxylic acid, monohydrochloride; 1-ethyl-6,8-difluoro-1,4-dihydro-4-oxo-7-[3-(4-pyridinyl)-1-piperazinyl]-3-quinolinecarboxylic acid; 1-cyclopropyl-6-fluoro-1,4-dihydro-4-oxo-7-[3(2-pyridinyl)-1-piperazinyl]-3-quinolinecarboxylic acid; and 1-cyclopropyl-6-fluoro-1,4-dihydro-4-oxo-7-[3-(2-pyridinyl)-1-piperazinyl]-3-quinolinecarboxylic acid, monohydrochloride.

7. A compound according to claim 1, 1-cyclopropyl-6-fluoro-7-[3-(fluoromethyl)-1-piperazinyl]-1,4-dihydro-4-oxo-3-quinolinecarboxylic acid.

8. A compound according to claim 1, 1-cyclopropyl-6-fluoro-7-[3-(difluoromethyl)-1-piperazinyl]-1,4-dihydro-4-oxo-3-quinolinecarboxylic acid.

9. A compound according to claim 1, 1-cyclopropyl-6-fluoro-7-[3-(trifluoromethyl)-1-piperazinyl]-1,4-dihydro-4-oxo-3-quinolinecarboxylic acid.

10. A compound 1-ethyl-5,6,8-trifluoro-1,4-dihydro-7-(3-methyl-1-piperazinyl)-4-oxo-3-quinolinecarboxylic acid.

11. The compound 1-cyclopropyl-5,6,8-trifluoro-1,4-dihydro-7-(4-methyl-1-piperazinyl)-4-oxo-3-quinolinecarboxylic acid.

* * * * *